United States Patent
Velten et al.

(10) Patent No.: US 8,563,584 B2
(45) Date of Patent: Oct. 22, 2013

(54) SUBSTITUTED ENAMINOTHIOCARBONYL COMPOUNDS

(75) Inventors: Robert Velten, Langenfeld (DE); Peter Jeschke, Bergisch Gladbach (DE); Eva-Maria Franken, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 209 days.

(21) Appl. No.: 12/934,001

(22) PCT Filed: Mar. 25, 2009

(86) PCT No.: PCT/EP2009/002164
§ 371 (c)(1),
(2), (4) Date: Oct. 27, 2010

(87) PCT Pub. No.: WO2009/121507
PCT Pub. Date: Oct. 8, 2009

(65) Prior Publication Data
US 2011/0039894 A1 Feb. 17, 2011

(30) Foreign Application Priority Data

Mar. 31, 2008 (EP) ..................................... 08153687

(51) Int. Cl.
*A01N 43/40* (2006.01)
*C07D 405/12* (2006.01)

(52) U.S. Cl.
USPC ....................................... 514/336; 546/284.4

(58) Field of Classification Search
USPC ....................................... 546/284.4; 514/336
See application file for complete search history.

(56) References Cited

U.S. PATENT DOCUMENTS

| 4,030,994 | A | 6/1977 | Kollonitsch |
| 4,195,036 | A | 3/1980 | Gozzo et al. |
| 4,748,243 | A | 5/1988 | Beck et al. |
| 4,778,896 | A | 10/1988 | Gallenkamp |
| 4,990,622 | A | 2/1991 | Jelich |
| 5,116,993 | A | 5/1992 | Jelich |
| 5,420,270 | A | 5/1995 | Chandrakumar et al. |
| 5,679,796 | A | 10/1997 | Kraatz |
| 5,811,555 | A | 9/1998 | Wakasugi et al. |
| 6,022,974 | A | 2/2000 | Werbitzky et al. |
| 6,252,087 | B1 | 6/2001 | Koch et al. |
| 7,417,150 | B2 | 8/2008 | Jeschke et al. |
| 2005/0009839 | A1 | 1/2005 | Jeshcke et al. |
| 2009/0247551 | A1 | 10/2009 | Jeschke et al. |
| 2009/0253749 | A1 | 10/2009 | Jeschke et al. |
| 2010/0048646 | A1 | 2/2010 | Jeschke et al. |

FOREIGN PATENT DOCUMENTS

| DE | 2747814 | 5/1978 |
| DE | 3314196 | 9/1983 |
| DE | 3630046 | 3/1988 |
| DE | 3631538 | 3/1988 |
| DE | 10 2006 015467 | 10/2007 |
| DE | 102006015468 | 10/2007 |
| EP | 104876 | 4/1984 |
| EP | 302389 | 2/1989 |
| EP | 373464 | 6/1990 |
| EP | 393453 | 10/1990 |
| EP | 446 913 | 9/1991 |
| EP | 0 539 588 | 5/1993 |
| EP | 569947 | 11/1993 |
| EP | 775700 | 5/1997 |
| EP | 780384 | 6/1997 |
| EP | 794180 | 9/1997 |
| JP | 05239034 | 9/1993 |
| WO | 8800183 | 1/1988 |
| WO | 9710226 | 3/1997 |
| WO | 01/07414 | 2/2001 |
| WO | 02/085870 | 10/2002 |
| WO | 02085870 | 10/2002 |
| WO | 2004/082616 | 9/2004 |
| WO | 2006/037475 | 4/2006 |
| WO | 2007/115644 | 10/2007 |
| WO | 2007/115646 | 10/2007 |
| WO | 2007115643 | 10/2007 |
| WO | 2008009360 | 1/2008 |

OTHER PUBLICATIONS

Dorwald, Side Reactions in Organic Synthesis, 2005, Wiley: VCH Weinheim Preface, pp. 1-15 & Chapter 8, pp. 279-308.*
International Search Report of PCT/EP2009/002164 dated Mar. 31, 2008 (13 pages).
Meerwein et al., Justus Liebigs Ann. Chem. 641, 1961, pp. 1-39.
Cabanal-Duvillard et al., "A Simple Access to Key Pyridine Building Blocks," Heterocycl. Commun., 1999, 5, pp. 257-262.
Pesti et al., "Efficient Pyridinylmethyl Functionalization: Synthesis of 10,10-Bis[(2-fluoro-4-pyridinyl)methyl]-9(10H)-anthracenone (DMP543), an Acetylcholine Release Enhancing Agent," J. Org. Chem., 2000, 65, pp. 7718-7722.
Gassen et al., "Fluorinated Cyclopropanecarboxylic Acids and Their Derivatives," Journal of Fluorine Chemistry, 1990, 49, pp. 127-139.
M. Moore, "The Leuckart Reaction," Organic Reactions, 1952, pp. 301-330, John Wiley & Sons, Inc., London).
Marvel et al., Organic Synthesis Collective vol. 3, 1955, pp. 366-367.
Metzner et al., "Sulfur Reagents in Organic Synthesis", B. Harcourt (ed.), 1994, p. 44-45, Academic Press, London.
Smith et al., "Conversion of Amides and Lactams to Thioamides and Thiolactams Using Hexamethyldisilathiane," Journal of Organic Chemistry,1994, 59, pp. 348-354.
R. Eibeck, "Inorganic Synthesis", 1963, pp. 128-131.
Crossland et al., "Facile synthesis of methanesulfonate esters," Journal of Organic Chemistry, 1970, 35, pp. 3195-3196.

(Continued)

*Primary Examiner* — Patricia L Morris
(74) *Attorney, Agent, or Firm* — Miles & Stockbridge PC

(57) ABSTRACT

The present application relates to novel substituted enaminothiocarbonyl compounds, to processes for their preparation and to their use for controlling animal pests, especially arthropods, in particular insects.

12 Claims, No Drawings

(56) References Cited

OTHER PUBLICATIONS

Labruere et al., "Efficient Syntheses of Thiono and Dithio Analogues of Tetronic Acid," Synthesis, 2006, No. 24, pp. 4163-4166, George Thieme Verlag Stuttgart, NY.

Roos et al., Organic Syntheses Coll. vol. I, (1941), pp. 145-147.

Ilankumaran et al., "A Facile Conversion of Amides and Lactams to Thioamides and Thiolactams using Tetrathiomolybdate," Tetrahedron Letters, 1995, vol. 36, No. 45, pp. 8311-8314, Elsevier Science Ltd.

Houben-Weyl, Methoden der Organischen Chemie, Bd. XI/1, 4. Aufl. 1957, Georg Thieme Verlag Stuttgart, S. 648.

Van Der Eycken, et al., "Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes," J. Chem. Soc., Perkin Trans. 2, 2002, pp. 928-937, The Royal Society of Chemistry 2002.

Wipf et al., "93. 2,4-Bis(4-methylphenylthio)-1,3,2$\lambda$5,4$\lambda$5-dithiadiphosphetan-2,4-dithion: Ein neues Reagens zur Schwefelung von N,N-disubstituierten Amiden," Helv. Chim. Acta; 1987; pp. 1001-1011; vol. 70.

S. Patai, "The Chemistry of Amino Group," 1968, Interscience Publishers, New York.

D. Brillon, "In Situ Reagents for Thionation of Amides, Peptides and Lactams," Synth. Commun., 1990, 20, pp. 3085-3095, Marcel Dekker, Inc.

Thomsen et al., "Thiation with 2,4-Bis(4-Methoxyphenyl)-1,3,2,4-Dithiadiphosphetane 2,4-Disulfide: N-Methylthiopyrrolidone (2-Pyrrolidinethione, 1-methyl-)," Org. Synth., 1984, 62, pp. 158-163.

Koester et al., "Sulfidierung ausgewaehlter Carbonsaeure- und Kohlensaeureamide mit dem (9-BBN)2S-Reagenz," Liebigs Ann. Chem., 1992, pp. 1081-1086.

Clausen et al., "Studies on Amino Acids and Peptides. Part 6. Methods for Introducing Thioamide Bonds into the Peptide Backbone: Synthesis of the Four Monothio Analogues of Leucine Enkephalin," J. Chem. Soc., Perkin Trans. I, 1984, pp. 785-798.

* cited by examiner

SUBSTITUTED ENAMINOTHIOCARBONYL COMPOUNDS

CROSS REFERENCE TO RELATED APPLICATIONS

This application is a §371 National Stage Application of PCT/EP2009/002164 filed Mar. 25, 2009, which claims priority to European Application 08153687.2 filed Mar. 31, 2008.

BACKGROUND OF THE INVENTION

1. Field of the Invention

The present application relates to novel substituted enaminothiocarbonyl compounds, to processes for their preparation and to their use for controlling animal pests, especially arthropods, in particular insects.

2. Description of Related Art

Certain substituted enaminothiocarbonyl compounds are already known as insecticidally active compounds (cf. EP 0 539 588 A1) or have been described as intermediates for preparing insecticidally active compounds (cf. WO 2002/085870 A1).

Modern crop protection agents have to satisfy many demands, for example with respect to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection agents cannot be considered as having been concluded, and there is a constant need for novel compounds having properties which, compared to the known compounds, are improved at least in respect of individual aspects.

SUMMARY OF THE INVENTION

It was an object of the present invention to provide compounds which broaden the spectrum of the pesticides under various aspects.

This object, and other objects not explicitly mentioned which can be derived or deduced from the context discussed here, is/are achieved by novel compounds of the formula (I),

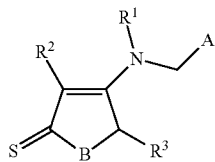

(I)

in which

A represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is optionally substituted in the 2-position by chlorine or methyl, or A represents a radical pyrimidinyl, pyrazolyl, thiophenyl, oxazolyl, isoxazolyl, 1,2,4-oxa-diazolyl, isothiazolyl, 1,2,4-triazolyl or 1,2,5-thiadiazolyl which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine) or $C_1$-$C_3$-alkylsulphonyl (which is optionally substituted by fluorine and/or chlorine), or A represents a radical

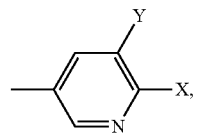

in which

X represents halogen, alkyl or haloalkyl,

Y represents halogen, alkyl, haloalkyl, haloalkoxy, azido or cyano,

B represents oxygen, sulphur or methylene, $R^1$ represents hydrogen, alkyl, haloalkyl, alkenyl, haloalkenyl, alkynyl, cycloalkyl, cycloalkylalkyl, halocycloalkyl, alkoxy or halo cycloalkylalkyl, $R^2$ represents hydrogen or halogen and $R^3$ represents hydrogen or alkyl, with the proviso that 4-{[(6-chloropyrid-3-yl)methyl](methyl)amino}furan-2(5H)-thione, 4-{[(6-chloropyrid-3-yl)methyl]amino}furan-2(5H)-thione, 4-{[(6-chloropyrid-3-yl)methyl]-(methyl)amino}thiophene-2(5H)-thione and 4-{[(6-chloropyrid-3-yl)methyl](ethyl)-amino}thiophene-2(5H)-thione are excluded.

DETAILED DESCRIPTION OF A PREFERRED EMBODIMENT

Furthermore, it has been found that the novel substituted compounds of the formula (I) are obtained when a) compounds of the formula (II)

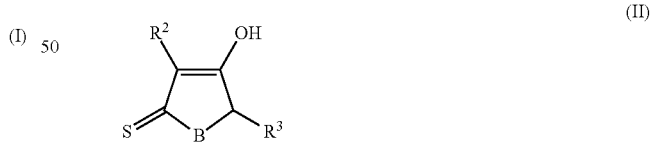

(II)

in which

B, $R^2$ and $R^3$ have the meanings mentioned further above are reacted with compounds of the formula (III)

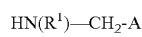

HN($R^1$)—$CH_2$-A    (III)

in which

A and $R^1$ have the meanings mentioned further above, if appropriate in the presence of a suitable diluent and if appropriate in the presence of an acidic auxiliary (Process 1), or when b) compounds of the formula (Ia)

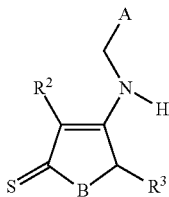

(Ia)

in which
A, B, R² and R³ have the meanings mentioned further above
are reacted with compounds of the formula (IV)

E-R¹ (IV)

in which
R¹ has the meanings mentioned further above and
E represents a suitable leaving group, such as, for example, halogen (in particular bromine, chlorine, iodine) or O-sulphonylalkyl and O-sulphonylaryl (in particular O-mesyl, O-tosyl),
if appropriate in the presence of a suitable diluent and if appropriate in the presence of an acid acceptor (Process 2), or when
c) compounds of the formula (II)

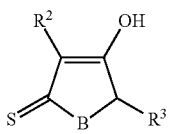

(II)

in which
B, R² and R³ have the meanings mentioned further above,
are, in a first reaction step, reacted with compounds of the formula (V)

H₂N—R¹ (V)

in which
R¹ has the meaning mentioned further above,
if appropriate in the presence of a suitable diluent and if appropriate in the presence of an acidic auxiliary and subsequently, in a second reaction step, the compounds of the formula (VI) formed

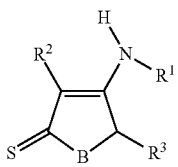

(VI)

in which
B, R¹, R² and R³ have the meanings mentioned further above,
are reacted with compounds of the formula (VII)

E-CH₂-A (VII)

in which
E and A have the meanings mentioned further above
if appropriate in the presence of a suitable diluent and if appropriate in the presence of an acid acceptor (Process 3).

Finally, it has been found that the novel compounds of the formula (I) have strongly pronounced biological properties and are suitable especially for controlling animal pests, in particular insects, arachnids and nematodes encountered in agriculture, in forests, in the protection of stored products and in the protection of materials, and also in the hygiene sector.

Depending, where appropriate, on the nature of the substituents, the compounds of the formula (I) may be present as geometrical and/or as optically active isomers or corresponding isomer mixtures of varying composition. The invention relates both to the pure isomers and to the isomer mixtures.

The formula (I) provides a general definition of the compounds according to the invention.

Preferred, particularly preferred and very particularly preferred substituents or ranges of the radicals listed in the formula (I) mentioned above are illustrated below.

A preferably represents 6-fluoropyrid-3-yl, 6-chloropyrid-3-yl, 6-bromopyrid-3-yl, 6-methyl-pyrid-3-yl, 6-trifluoromethyl-pyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl.

B preferably represents oxygen.
R¹ preferably represents optionally fluorine-substituted $C_1$-$C_5$-alkyl, $C_2$-$C_5$-alkenyl, $C_3$-$C_5$-cycloalkyl or $C_3$-$C_5$-cycloalkylalkyl.
R² preferably represents hydrogen or halogen.
R³ preferably represents hydrogen or methyl.
A particularly preferably represents the radical 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.
B particularly preferably represents oxygen.
R¹ particularly preferably represents methyl, ethyl, propyl, vinyl, allyl, propargyl, cyclo-propyl, 2-fluoroethyl, 2,2-difluoroethyl or 2-fluorocyclopropyl.
R² particularly preferably represents hydrogen, fluorine or chlorine.
R³ particularly preferably represents hydrogen.
B very particularly preferably represents oxygen.
A very particularly preferably represents the radical 6-chloropyrid-3-yl, 6-bromopyrid-3-yl, or 6-chloro-1,4-pyridazin-3-yl, 5-fluoro-6-chloropyrid-3-yl or 5-fluoro-6-bromopyrid-3-yl.

R¹ very particularly preferably represents methyl, ethyl, n-propyl, n-prop-2-enyl, n-prop-2-ynyl, cyclopropyl, 2-fluoroethyl or 2,2-difluoroethyl.

R² very particularly preferably represents hydrogen.

R³ very particularly preferably represents hydrogen.

In a special group of compounds of the formula (I), A represents 6-fluoropyrid-3-yl

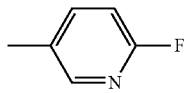

In a special group of compounds of the formula (I), A represents 6-chloropyrid-3-yl

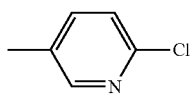

In a further special group of compounds of the formula (I), A represents 6-bromopyrid-3-yl

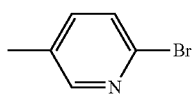

In a further special group of compounds of the formula (I), A represents 6-trifluoromethylpyrid-3-yl

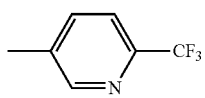

In a further special group of compounds of the formula (I), A represents 6-chloro-1,4-pyridazin-3-yl

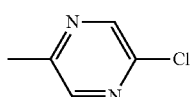

In a further special group of compounds of the formula (I), A represents 2-chloro-1,3-thiazol-5-yl

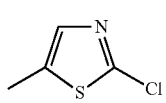

A further group of preferred compounds of the formula (I) is defined hereinbelow, where A represents pyrid-3-yl which is substituted in the 6-position by fluorine, chlorine, bromine, methyl or trifluoromethyl or represents 2-chloropyrazin-5-yl or represents 2-chloro-1,3-thiazol-5-yl, B represents oxygen, R¹ represents halo-$C_{1-3}$-alkyl, halo-$C_{2-3}$-alkenyl, halocyclopropyl (where halogen represents in particular fluorine or chlorine), R² represents hydrogen or halogen, R³ represents hydrogen or methyl, A preferably represents 6-fluoropyrid-3-yl, 6-chloropyrid-3-yl, 6-bromopyrid-3-yl, 6-trifluoromethylpyrid-3-yl, 2-chloropyrazin-5-yl or 2-chloro-1,3-thiazol-5-yl, B preferably represents oxygen, R¹ preferably represents difluoromethyl, 2-fluoroethyl, 2,2-difluoroethyl, 2-chloro-2-fluoroethyl, 3-fluoro-n-propyl, 2-fluorovinyl, 3,3-difluoroprop-2-enyl or 3,3-dichloroprop-2-enyl, R² preferably represents hydrogen or halogen (where halogen represents in particular fluorine or chlorine), R³ preferably represents hydrogen, A particularly preferably represents the radical 6-chloropyrid-3-yl or 6-bromopyrid-3-yl, B particularly preferably represents oxygen, R¹ particularly preferably represents 2-fluoroethyl or 2,2-difluoroethyl, R² particularly preferably represents hydrogen, R³ particularly preferably represents hydrogen, A very particularly preferably represents the radical 6-chloropyrid-3-yl or 6-bromopyrid-3-yl, B very particularly preferably represents oxygen, R¹ very particularly preferably represents 2,2-difluoroethyl, R² very particularly preferably represents hydrogen and R³ very particularly preferably represents hydrogen.

In a further special group of compounds of the formula (I), R³ represents hydrogen, B represents oxygen and A represents 6-chloropyrid-3-yl

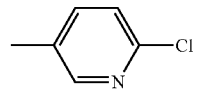

In a further special group of compounds of the formula (I), R³ represents hydrogen, B represents oxygen and A represents 6-bromopyrid-3-yl

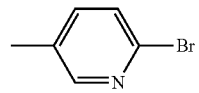

In a further special group of compounds of the formula (I), R³ represents hydrogen, B represents oxygen and A represents 6-fluoropyrid-3-yl

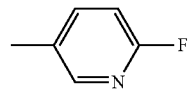

In a further special group of compounds of the formula (I), R³ represents hydrogen, B represents oxygen and A represents 6-trifluoromethylpyrid-3-yl

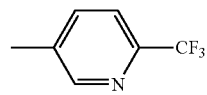

In a further special group of compounds of the formula (I), R³ represents hydrogen, B represents oxygen and A represents 2-chloro-1,3-thiazol-5-yl

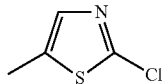

In a further special group of compounds of the formula (I), R² and R³ represent hydrogen, B represents oxygen and A represents 6-chloropyrid-3-yl

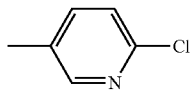

In a further special group of compounds of the formula (I), R² and R³ represent hydrogen, B represents oxygen and A represents 6-bromopyrid-3-yl

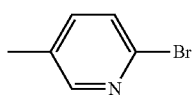

In a further special group of compounds of the formula (I), R² and R³ represent hydrogen, B represents oxygen and A represents 6-fluoropyrid-3-yl

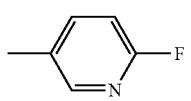

In a further special group of compounds of the formula (I), R² and R³ represent hydrogen, B represents oxygen and A represents 6-trifluoromethylpyrid-3-yl

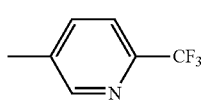

In a further special group of compounds of the formula (I), R² and R³ represent hydrogen, B represents oxygen and A represents 2-chloro-1,3-thiazol-5-yl

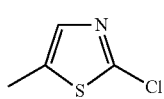

In a further special group of compounds of the formula (I), R¹ represents difluoromethyl, R² and R³ represent hydrogen and B represents oxygen.

In a further special group of compounds of the formula (I), R¹ represents 2-fluoroethyl, R² and R³ represent hydrogen and B represents oxygen.

In a further special group of compounds of the formula (I), R¹ represents 2,2-difluoroethyl, R² and R³ represent hydrogen and B represents oxygen.

The general or preferred radical definitions or illustrations given above can be combined with one another as desired, i.e. including combinations between the respective preferred ranges.

Preference according to the invention is given to compounds of the formula (I) which contain a combination of the meanings listed above as being preferred.

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

A preferred sub-group of the enaminothiocarbonyl compounds according to the invention are those of the formula (I-a)

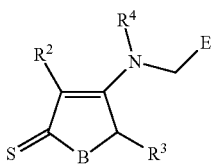

(I-a)

in which

E represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is optionally substituted in the 2-position by chlorine or methyl, R⁴ represents haloalkyl, haloalkenyl, halocycloalkyl or halocycloalkylalkyl, and R², R³ and B have the meanings given above.

Preferred substituents or ranges of the radicals listed in the formula (I-a) mentioned above and below are illustrated below.

E preferably represents 6-fluoropyrid-3-yl, 6-chloropyrid-3-yl, 6-bromopyrid-3-yl, 6-methyl-pyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl.

B preferably represents oxygen.

R² preferably represents hydrogen or halogen (where halogen represents in particular fluorine or chlorine).

R³ preferably represents hydrogen or methyl.

R⁴ preferably represents fluorine-substituted C₁-C₅-alkyl, C₂-C₅-alkenyl, C₃-C₅-cycloalkyl or C₃-C₅-cycloalkylalkyl.

E particularly preferably represents the radical 6-fluoropyrid-3-yl, 6-chloropyrid-3-yl, 6-bromopyrid-3-yl, 6-chloro-1,4-pyridazin-3-yl, 2-chloro-1,3-thiazol-5-yl.

B particularly preferably represents oxygen.

R² particularly preferably represents hydrogen.

R³ particularly preferably represents hydrogen.

R⁴ particularly preferably represents 2-fluoroethyl, 2,2-difluoroethyl, 2-fluorocyclopropyl.

E very particularly preferably represents the radical 6-chloropyrid-3-yl, 6-bromopyrid-3-yl, or 6-chloro-1,4-pyridazin-3-yl.

B very particularly preferably represents oxygen.
$R^2$ very particularly preferably represents hydrogen.
$R^3$ very particularly preferably represents hydrogen.
$R^4$ very particularly preferably represents 2,2-difluoroethyl.

In a special group of compounds of the formula (I-a), E represents 6-chloropyrid-3-yl

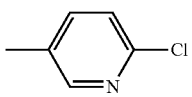

In a further special group of compounds of the formula (I-a), E represents 6-bromopyrid-3-yl

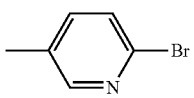

In a further special group of compounds of the formula (I-a), E represents 6-chloro-1,4-pyridazin-3-yl

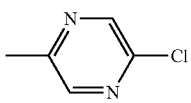

In a further special group of compounds of the formula (I-a), E represents 2-chloro-1,3-thiazol-5-yl

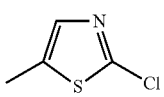

A further group of preferred compounds of the formula (I-a) is defined hereinbelow, where
E represents pyrid-3-yl which is substituted in the 6-position by fluorine, chlorine, bromine, methyl or trifluoromethyl or represents 2-chloropyrazin-5-yl or represents 2-chloro-1,3-thiazol-5-yl,
B represents oxygen, sulphur or methylene,
$R^2$ represents hydrogen or halogen,
$R^3$ represents hydrogen or methyl,
$R^4$ represents halo-$C_{1-3}$-alkyl, halo-$C_{2-3}$-alkenyl, halocyclopropyl (where halogen represents in particular fluorine or chlorine),
E preferably represents 6-fluoropyrid-3-yl, 6-chloropyrid-3-yl, 6-bromopyrid-3-yl, 6-trifluoromethylpyrid-3-yl, 2-chloropyrazin-5-yl or 2-chloro-1,3-thiazol-5-yl,
B preferably represents oxygen,
$R^2$ preferably represents hydrogen or halogen (where halogen represents in particular fluorine or chlorine),
$R^3$ preferably represents hydrogen,
$R^4$ preferably represents difluoromethyl, 2-fluoroethyl, 2,2-difluoroethyl, 2-chloro-2-fluoroethyl, 3-fluoro-n-propyl, 2-fluorovinyl, 3,3-difluoroprop-2-enyl or 3,3-dichloroprop-2-enyl,
E particularly preferably represents the radical 6-chloropyrid-3-yl or 6-bromopyrid-3-yl,
B particularly preferably represents oxygen,
$R^2$ particularly preferably represents hydrogen,
$R^3$ particularly preferably represents hydrogen,
$R^4$ particularly preferably represents 2-fluoroethyl or 2,2-difluoroethyl,
E very particularly preferably represents the radical 6-chloropyrid-3-yl or 6-bromopyrid-3-yl,
B very particularly preferably represents oxygen,
$R^2$ very particularly preferably represents hydrogen,
$R^3$ very particularly preferably represents hydrogen and
$R^4$ very particularly preferably represents 2,2-difluoroethyl.

In a special group of compounds of the formula (I-a), $R^3$ represents hydrogen, B represents oxygen and E represents 6-chloropyrid-3-yl

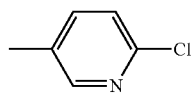

In a further special group of compounds of the formula (I-a), $R^3$ represents hydrogen, B represents oxygen and E represents 6-bromopyrid-3-yl

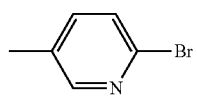

In a further special group of compounds of the formula (I-a), $R^3$ represents hydrogen, B represents oxygen and E represents 6-fluoropyrid-3-yl

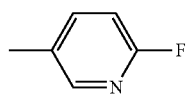

In a further special group of compounds of the formula (I-a), $R^3$ represents hydrogen, B represents oxygen and E represents 6-trifluoromethylpyrid-3-yl

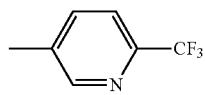

In a further special group of compounds of the formula (I-a), $R^3$ represents hydrogen, B represents oxygen and E represents 2-chloro-1,3-thiazol-5-yl

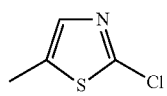

In a further special group of compounds of the formula (I-a), $R^2$ and $R^3$ represent hydrogen, B represents oxygen and E represents 6-chloropyrid-3-yl

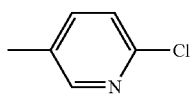

In a further special group of compounds of the formula (I-a), $R^2$ and $R^3$ represent hydrogen, B represents oxygen and E represents 6-bromopyrid-3-yl

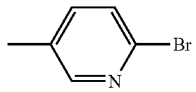

In a further special group of compounds of the formula (I-a), $R^2$ and $R^3$ represent hydrogen, B represents oxygen and E represents 6-fluoropyrid-3-yl

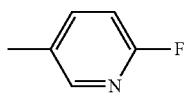

In a further special group of compounds of the formula (I-a), $R^2$ and $R^3$ represent hydrogen, B represents oxygen and E represents 6-trifluoromethylpyrid-3-yl

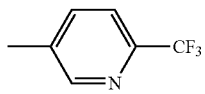

In a further special group of compounds of the formula (I-a), $R^2$ and $R^3$ represent hydrogen, B represents oxygen and E represents 2-chloro-1,3-thiazol-5-yl

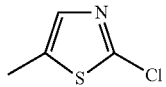

In a further special group of compounds of the formula (I-a), $R^4$ represents difluoromethyl, $R^2$ and $R^3$ represent hydrogen and B represents oxygen.

In a further special group of compounds of the formula (I-a), $R^4$ represents 2-fluoroethyl, $R^2$ and $R^3$ represent hydrogen and B represents oxygen.

In a further special group of compounds of the formula (I-a), $R^4$ represents 2,2-difluoroethyl, $R^2$ and $R^3$ represent hydrogen and B represents oxygen.

A further preferred sub-group of the enaminothiocarbonyl compounds according to the invention are those of the formula (I-b)

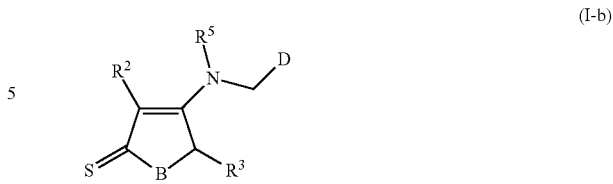

in which
D represents a radical pyrimidinyl, pyrazolyl, thiophenyl, oxazolyl, isoxazolyl, 1,2,4-oxa-diazolyl, isothiazolyl, 1,2,4-triazolyl or 1,2,5-thiadiazolyl which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine) or $C_1$-$C_3$-alkylsulphonyl (which is optionally substituted by fluorine and/or chlorine),
or
D represents a radical

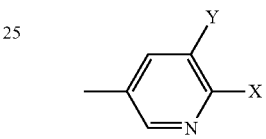

in which
X and Y have the meanings given above,
$R^5$ represents hydrogen, alkyl, alkenyl, alkynyl, cycloalkyl or alkoxy,
and $R^2$, $R^3$ and B have the meanings given above.

Preferred substituents or ranges of the radicals listed in the formula (I-b) mentioned above and below are illustrated below.

D preferably represents 2-chloropyrimidin-5-yl or 2-trifluoromethylpyrimidin-5-yl, furthermore
D preferably represents one of the radicals 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl, 5-difluoromethyl-6-iodopyrid-3-yl.
B preferably represents oxygen.
$R^2$ preferably represents hydrogen or halogen (where halogen represents in particular fluorine or chlorine).
$R^3$ preferably represents hydrogen.
$R^5$ preferably and particularly preferably represents $C_1$-$C_4$-alkyl, $C_2$-$C_4$-alkenyl, $C_2$-$C_4$-alkynyl or $C_3$-$C_4$-cycloalkyl.
D particularly preferably represents 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.
B particularly preferably represents oxygen.

$R^2$ particularly preferably represents hydrogen.
$R^3$ particularly preferably represents hydrogen.
D very particularly preferably represents 5-fluoro-6-chloropyrid-3-yl or 5-fluoro-6-bromopyrid-3-yl.
B very particularly preferably represents oxygen.
$R^2$ very particularly preferably represents hydrogen.
$R^3$ very particularly preferably represents hydrogen.
$R^5$ very particularly preferably represents methyl, ethyl, propyl, vinyl, allyl, propargyl or cyclopropyl.

In a special group of compounds of the formula (I-b), $R^3$ represents hydrogen, B represents oxygen and D represents 2-chloropyrimidin-5-yl,

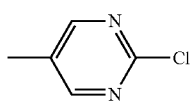

In a further special group of compounds of the formula (I-b), $R^3$ represents hydrogen, B represents oxygen and D represents 5-fluoro-6-chloropyrid-3-yl,

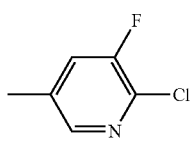

In a further special group of compounds of the formula (I-b), $R^3$ represents hydrogen, B represents oxygen and D represents 5,6-dichloropyrid-3-yl

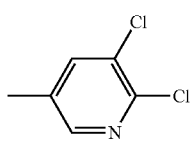

In a further special group of compounds of the formula (I-b), $R^3$ represents hydrogen, B represents oxygen and D represents 5-bromo-6-chloropyrid-3-yl

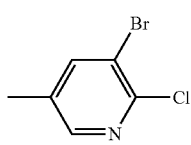

In a further special group of compounds of the formula (I-b), $R^3$ represents hydrogen, B represents oxygen and D represents 5-methyl-6-chloropyrid-3-yl

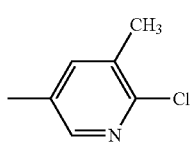

In a further special group of compounds of the formula (I-b), $R^3$ represents hydrogen, B represents oxygen and D represents 5-fluoro-6-bromopyrid-3-yl

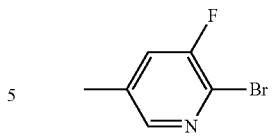

In a further special group of compounds of the formula (I-b), $R^3$ represents hydrogen, B represents oxygen and D represents 5-chloro-6-bromopyrid-3-yl

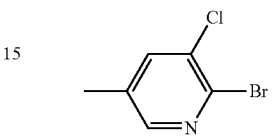

In a further special group of compounds of the formula (I-b), $R^3$ represents hydrogen, B represents oxygen and D represents 5-chloro-6-iodopyrid-3-yl

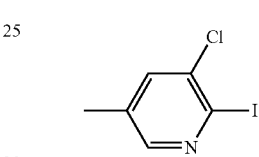

In a special group of compounds of the formula (I-b), $R^2$ and $R^3$ represent hydrogen, B represents oxygen and D represents 2-chloropyrimidin-5-yl,

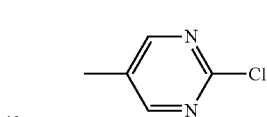

In a further special group of compounds of the formula (I-b), $R^2$ and $R^3$ represent hydrogen, B represents oxygen and D represents 5-fluoro-6-chloropyrid-3-yl,

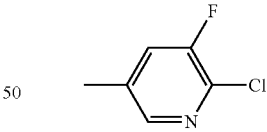

In a further special group of compounds of the formula (I-b), $R^2$ and $R^3$ represent hydrogen, B represents oxygen and D represents 5,6-dichloropyrid-3-yl

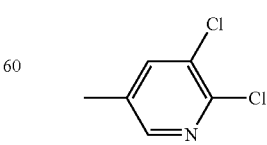

In a further special group of compounds of the formula (I-b), $R^2$ and $R^3$ represent hydrogen, B represents oxygen and D represents 5-bromo-6-chloropyrid-3-yl

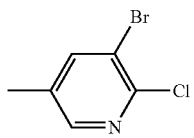

In a further special group of compounds of the formula (I-b), $R^2$ and $R^3$ represent hydrogen, B represents oxygen and D represents 5-methyl-6-chloropyrid-3-yl

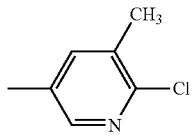

In a further special group of compounds of the formula (I-b), $R^2$ and $R^3$ represent hydrogen, B represents oxygen and D represents 5-fluoro-6-bromopyrid-3-yl

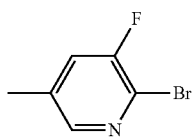

In a further special group of compounds of the formula (I-b), $R^2$ and $R^3$ represent hydrogen, B represents oxygen and D represents 5-chloro-6-bromopyrid-3-yl

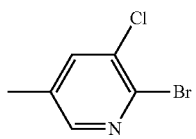

In a further special group of compounds of the formula (I-b), $R^2$ and $R^3$ represent hydrogen, B represents oxygen and D represents 5-chloro-6-iodopyrid-3-yl

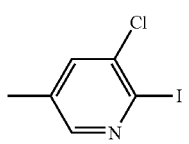

In a further special group of compounds of the formula (I-b), $R^5$ represents methyl, $R^2$ and $R^3$ represent hydrogen and B represents oxygen.

In a further special group of compounds of the formula (I-b), $R^5$ represents ethyl, $R^2$ and $R^3$ represent hydrogen and B represents oxygen.

In a further special group of compounds of the formula (I-b), $R^5$ represents cyclopropyl, $R^2$ and $R^3$ represent hydrogen and B represents oxygen.

A further preferred sub-group of the enaminothiocarbonyl compounds according to the invention are those of the formula (I-c)

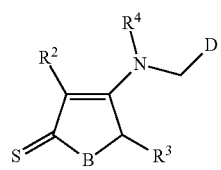

in which
D represents a radical pyrimidinyl, pyrazolyl, thiophenyl, oxazolyl, isoxazolyl, 1,2,4-oxa-diazolyl, isothiazolyl, 1,2,4-triazolyl or 1,2,5-thiadiazolyl which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine) or $C_1$-$C_3$-alkylsulphonyl (which is optionally substituted by fluorine and/or chlorine),
or
D represents a radical

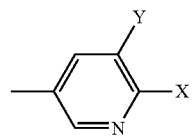

in which
X and Y have the meanings given above,
$R^4$ represents haloalkyl, haloalkenyl, halocycloalkyl or halocycloalkylalkyl,
and $R^2$, $R^3$ and B have the meanings given above.

Preferred substituents or ranges of the radicals listed in the formula (I-c) mentioned above and below are illustrated below.

D preferably represents 2-chloropyrimidin-5-yl or 2-trifluoromethylpyrimidin-5-yl,
furthermore
D preferably represents one of the radicals 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl, 5-difluoromethyl-6-iodopyrid-3-yl.

B preferably represents oxygen.
$R^2$ preferably represents hydrogen or halogen (where halogen represents in particular fluorine or chlorine).
$R^3$ preferably represents hydrogen.
$R^4$ preferably represents fluorine-substituted $C_1$-$C_5$-alkyl, $C_2$-$C_5$-alkenyl, $C_3$-$C_5$-cycloalkyl or $C_3$-$C_5$-cycloalkylalkyl.
D particularly preferably represents 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.

B particularly preferably represents oxygen.

R² particularly preferably represents hydrogen.

R³ particularly preferably represents hydrogen.

R⁴ particularly preferably represents 2-fluoroethyl, 2,2-difluoroethyl, 2-fluorocyclopropyl.

D very particularly preferably represents 5-fluoro-6-chloropyrid-3-yl or 5-fluoro-6-bromopyrid-3-yl.

B very particularly preferably represents oxygen.

R² very particularly preferably represents hydrogen.

R³ very particularly preferably represents hydrogen.

R⁴ very particularly preferably represents 2,2-difluoroethyl.

In a special group of compounds of the formula (I-c), R³ represents hydrogen, B represents oxygen and D represents 2-chloropyrimidin-5-yl,

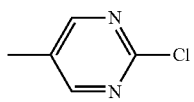

In a further special group of compounds of the formula (I-c), R³ represents hydrogen, B represents oxygen and D represents 5-fluoro-6-chloropyrid-3-yl,

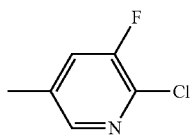

In a further special group of compounds of the formula (I-c), R³ represents hydrogen, B represents oxygen and D represents 5,6-dichloropyrid-3-yl

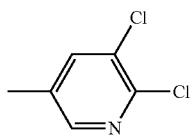

In a further special group of compounds of the formula (I-c), R³ represents hydrogen, B represents oxygen and D represents 5-bromo-6-chloropyrid-3-yl

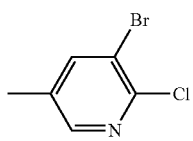

In a further special group of compounds of the formula (I-c), R³ represents hydrogen, B represents oxygen and D represents 5-methyl-6-chloropyrid-3-yl

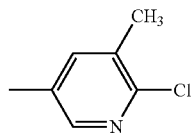

In a further special group of compounds of the formula (I-c), R³ represents hydrogen, B represents oxygen and D represents 5-fluoro-6-bromopyrid-3-yl

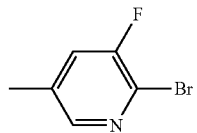

In a further special group of compounds of the formula (I-c), R³ represents hydrogen, B represents oxygen and D represents 5-chloro-6-bromopyrid-3-yl

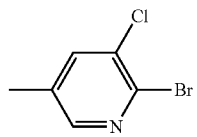

In a further special group of compounds of the formula (I-c), R³ represents hydrogen, B represents oxygen and D represents 5-chloro-6-iodopyrid-3-yl

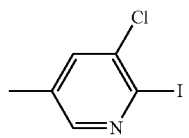

In a special group of compounds of the formula (I-c), R² and R³ represent hydrogen, B represents oxygen and D represents 2-chloropyrimidin-5-yl,

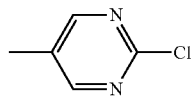

In a further special group of compounds of the formula (I-c), R² and R³ represent hydrogen, B represents oxygen and D represents 5-fluoro-6-chloropyrid-3-yl,

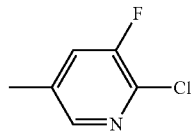

In a further special group of compounds of the formula (I-c), R² and R³ represent hydrogen, B represents oxygen and D represents 5,6-dichloropyrid-3-yl

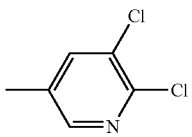

In a further special group of compounds of the formula (I-c), $R^2$ and $R^3$ represent hydrogen, B represents oxygen and D represents 5-bromo-6-chloropyrid-3-yl

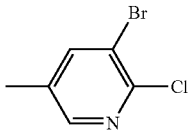

In a further special group of compounds of the formula (I-c), $R^2$ and $R^3$ represent hydrogen, B represents oxygen and D represents 5-methyl-6-chloropyrid-3-yl

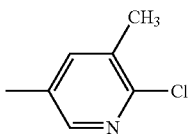

In a further special group of compounds of the formula (I-c), $R^2$ and $R^3$ represent hydrogen, B represents oxygen and D represents 5-fluoro-6-bromopyrid-3-yl

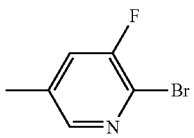

In a further special group of compounds of the formula (I-c), $R^2$ and $R^3$ represent hydrogen, B represents oxygen and D represents 5-chloro-6-bromopyrid-3-yl

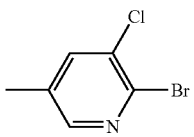

In a further special group of compounds of the formula (I-c), $R^2$ and $R^3$ represent hydrogen, B represents oxygen and D represents 5-chloro-6-iodopyrid-3-yl

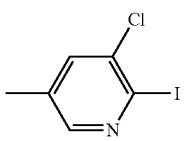

In a further special group of compounds of the formula (I-c), $R^4$ represents difluoromethyl, $R^2$ and $R^3$ represent hydrogen and B represents oxygen.

In a further special group of compounds of the formula (I-c), $R^4$ represents 2-fluoroethyl, $R^2$ and $R^3$ represent hydrogen and B represents oxygen.

In a further special group of compounds of the formula (I-c), $R^4$ represents 2,2-difluoroethyl, $R^2$ and $R^3$ represent hydrogen and B represents oxygen A preferred sub-group of the enaminothiocarbonyl compounds according to the invention are those of the formula (I-d)

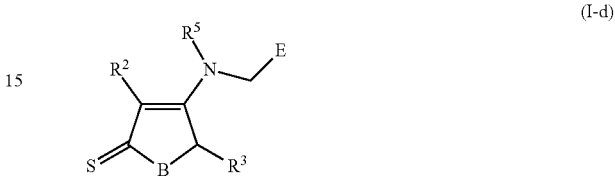

in which

E represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is optionally substituted in the 2-position by chlorine or methyl, $R^5$ represents $C_2$-$C_4$-alkyl, alkenyl, alkynyl, cycloalkyl or alkoxy, and $R^2$, $R^3$ and B have the meanings given above.

Preferred substituents or ranges of the radicals listed in the formula (I-d) mentioned above and below are illustrated below.

E preferably represents 6-fluoropyrid-3-yl, 6-chloropyrid-3-yl, 6-bromopyrid-3-yl, 6-methyl-pyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl.

B preferably represents oxygen or methylene.

$R^2$ preferably represents hydrogen or halogen (where halogen represents in particular fluorine or chlorine), $R^3$ preferably represents hydrogen or methyl.

$R^5$ preferably represents $C_2$-$C_4$-alkyl, $C_2$-$C_4$-alkenyl, $C_2$-$C_4$-alkynyl or $C_3$-$C_4$-cycloalkyl.

E particularly preferably represents the radical 6-fluoropyrid-3-yl, 6-chloropyrid-3-yl, 6-bromopyrid-3-yl, 6-chloro-1,4-pyridazin-3-yl, 2-chloro-1,3-thiazol-5-yl, B particularly preferably represents oxygen or methylene.

$R^2$ particularly preferably represents hydrogen.

$R^3$ particularly preferably represents hydrogen.

$R^5$ particularly preferably represents ethyl, propyl, vinyl, allyl, propargyl or cyclopropyl.

E very particularly preferably represents the radical 6-chloropyrid-3-yl, 6-bromopyrid-3-yl or 6-chloro-1,4-pyridazin-3-yl, B very particularly preferably represents oxygen.

$R^2$ very particularly preferably represents hydrogen.

$R^3$ very particularly preferably represents hydrogen.

$R^5$ very particularly preferably represents ethyl or cyclopropyl.

In a special group of compounds of the formula (I-d), E represents 6-chloropyrid-3-yl

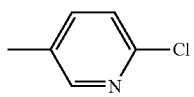

In a further special group of compounds of the formula (I-d), E represents 6-bromopyrid-3-yl

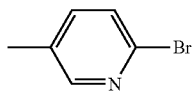

In a further special group of compounds of the formula (I-d), E represents 6-chloro-1,4-pyridazin-3-yl

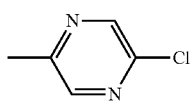

In a further special group of compounds of the formula (I-d), E represents 2-chloro-1,3-thiazol-5-yl

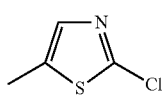

A further group of preferred compounds of the formula (I-d) is defined hereinbelow, where
- E represents pyrid-3-yl which is substituted in the 6-position by fluorine, chlorine, bromine, methyl or trifluoromethyl or represents 2-chloropyrazin-5-yl or represents 2-chloro-1,3-thiazol-5-yl,
- B represents oxygen, sulphur or methylene,
- $R^2$ represents hydrogen or halogen,
- $R^3$ represents hydrogen or methyl,
- $R^5$ represents $C_2$-$C_4$-alkyl, alkenyl, alkynyl, cycloalkyl or alkoxy,
- E preferably represents 6-fluoropyrid-3-yl, 6-chloropyrid-3-yl, 6-bromopyrid-3-yl, 6-trifluoromethylpyrid-3-yl, 2-chloropyrazin-5-yl or 2-chloro-1,3-thiazol-5-yl,
- B preferably represents oxygen,
- $R^2$ preferably represents hydrogen or halogen (where halogen represents in particular fluorine or chlorine),
- $R^3$ preferably represents hydrogen,
- $R^5$ preferably represents $C_2$-$C_4$-alkyl, $C_2$-$C_4$-alkenyl, $C_2$-$C_4$-alkynyl or $C_3$-$C_4$-cycloalkyl,
- E particularly preferably represents the radical 6-chloropyrid-3-yl or 6-bromopyrid-3-yl,
- B particularly preferably represents oxygen,
- $R^2$ particularly preferably represents hydrogen,
- $R^3$ particularly preferably represents hydrogen,
- $R^5$ particularly preferably represents ethyl, propyl, vinyl, allyl, propargyl or cyclopropyl,
- E very particularly preferably represents the radical 6-chloropyrid-3-yl or 6-bromopyrid-3-yl,
- B very particularly preferably represents oxygen,
- $R^2$ very particularly preferably represents hydrogen,
- $R^3$ very particularly preferably represents hydrogen and
- $R^5$ very particularly preferably represents ethyl or cyclopropyl.

In a special group of compounds of the formula (I-d), $R^3$ represents hydrogen, B represents oxygen and E represents 6-chloropyrid-3-yl

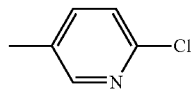

In a further special group of compounds of the formula (I-d), $R^3$ represents hydrogen, B represents oxygen and E represents 6-bromopyrid-3-yl

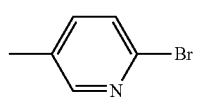

In a further special group of compounds of the formula (I-d), $R^3$ represents hydrogen, B represents oxygen and E represents 6-fluoropyrid-3-yl

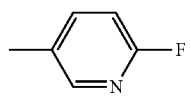

In a further special group of compounds of the formula (I-d), $R^3$ represents hydrogen, B represents oxygen and E represents 6-trifluoromethylpyrid-3-yl

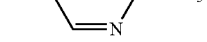

In a further special group of compounds of the formula (I-d), $R^3$ represents hydrogen, B represents oxygen and E represents 2-chloro-1,3-thiazol-5-yl

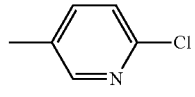

In a further special group of compounds of the formula (I-d), $R^2$ and $R^3$ represent hydrogen, B represents oxygen and E represents 6-chloropyrid-3-yl

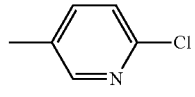

In a further special group of compounds of the formula (I-d), $R^2$ and $R^3$ represent hydrogen, B represents oxygen and E represents 6-bromopyrid-3-yl

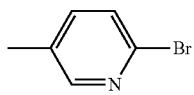

In a further special group of compounds of the formula (I-d), $R^2$ and $R^3$ represent hydrogen, B represents oxygen and E represents 6-fluoropyrid-3-yl

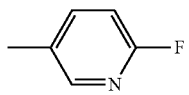

In a further special group of compounds of the formula (I-d), $R^2$ and $R^3$ represent hydrogen, B represents oxygen and E represents 6-trifluoromethylpyrid-3-yl

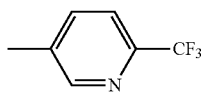

In a further special group of compounds of the formula (I-d), $R^2$ and $R^3$ represent hydrogen, B represents oxygen and E represents 2-chloro-1,3-thiazol-5-yl

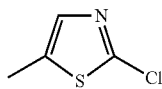

In a further special group of compounds of the formula (I-d), $R^5$ represents ethyl, $R^2$ and $R^3$ represent hydrogen and B represents oxygen.

In a further special group of compounds of the formula (I-d), $R^5$ represents cyclopropyl, $R^2$ and $R^3$ represent hydrogen and B represents oxygen.

Specific mention may be made of the following compounds of the general formula (I):

compound (I-1), 4-{[(6-bromopyrid-3-yl)methyl](2-fluoroethyl)amino}furan-2(5H)-thione, has the formula

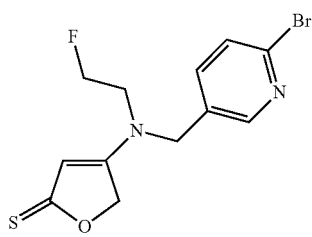 [SMILES: FCCN(Cc1ccc(Br)nc1)C1=CC(=S)OC1]

compound (I-2), 4-{[(6-bromopyrid-3-yl)methyl](2,2-difluoroethyl)amino}furan-2(5H)-thione, has the formula

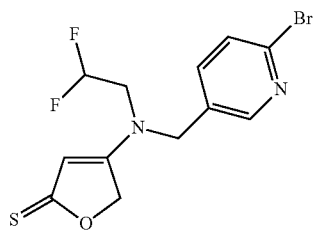 [SMILES: FC(F)CN(Cc1ccc(Br)nc1)C1=CC(=S)OC1]

compound (I-3), 4-{[(6-fluoropyrid-3-yl)methyl](2,2-difluoroethyl)amino}furan-2(5H)-thione, has the formula

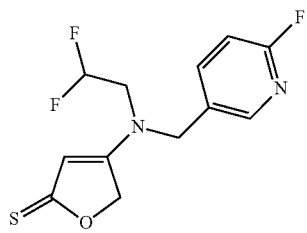 [SMILES: Fc1ccc(CN(CC(F)F)C2=CC(=S)OC2)cn1]

compound (I-4), 4-{[(2-chloro-1,3-thiazol-5-yl)methyl](2-fluoroethyl)amino}furan-2(5H)-thione, has the formula

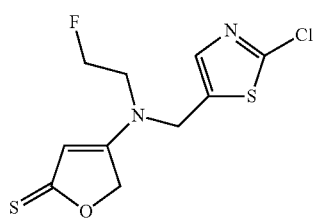 [SMILES: FCCN(Cc1cnc(Cl)s1)C1=CC(=S)OC1]

compound (I-5), 3-chloro-4-{[(6-chloropyrid-3-yl)methyl](2-fluoroethyl)amino}furan-2(5H)-thione, has the formula

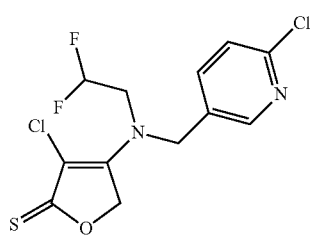 [SMILES: FC(F)CN(Cc1ccc(Cl)nc1)C1=C(Cl)C(=S)OC1]

compound (I-6), 4-{[(6-chloropyrid-3-yl)methyl](2-fluoroethyl)amino}furan-2(5H)-thione, has the formula

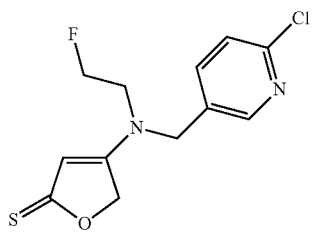 [SMILES: FCCN(Cc1ccc(Cl)nc1)C1=CC(=S)OC1]

compound (I-7), 4-{[(6-chloropyrid-3-yl)methyl](2,2-difluoroethyl)amino}furan-2(5H)-thione, has the formula

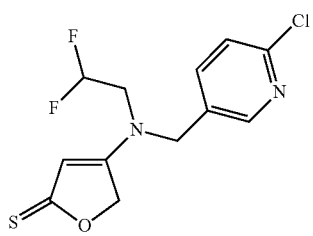

compound (I-8), 4-{[(6-chloro-5-fluoropyrid-3-yl)methyl](methyl)amino}furan-2(5H)-thione, has the formula

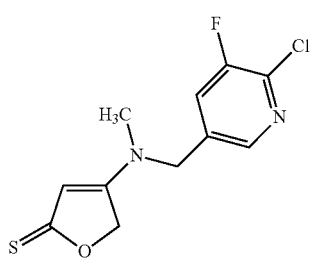 [SMILES: CN(Cc1cnc(Cl)c(F)c1)C1=CC(=S)OC1]

compound (I-9), 4-{[(5,6-dichloropyrid-3-yl)methyl](cyclopropyl)amino}furan-2(5H)-thione, has the formula

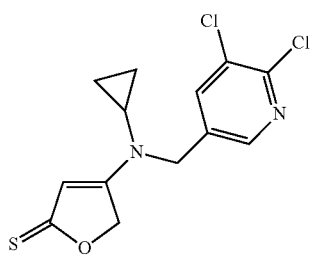 [SMILES: Fc1cc(CN(C2=CC(=S)OC2)C2CC2)cnc1Cl]

compound (I-10), 4-{[(5,6-dichloropyrid-3-yl)methyl](methyl)amino}furan-2(5H)-thione, has the formula

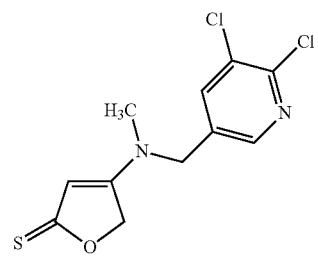

compound (I-11), 4-{[(6-bromo-5-fluoropyrid-3-yl)methyl](methyl)amino}furan-2(5H)-thione, has the formula

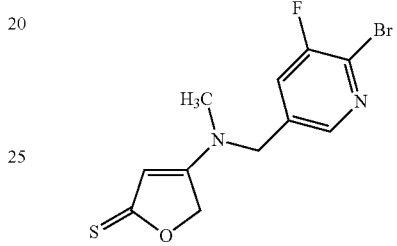

compound (I-12), 4-{[(6-bromo-5-fluoropyrid-3-yl)methyl](cyclopropyl)amino}furan-2(5H)-thione, has the formula

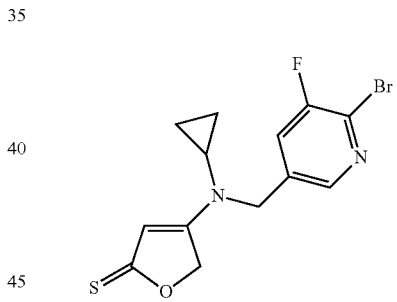

compound (I-13), 4-{[(6-chloro-5-fluoropyrid-3-yl)methyl](cyclopropyl)amino}furan-2(5H)-thione, has the formula

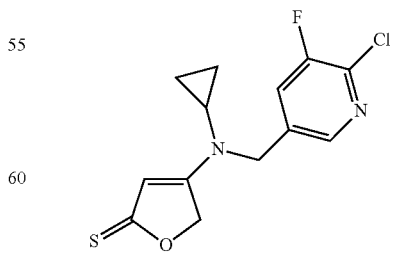

compound (I-14), 4-{[(5,6-dichloropyrid-3-yl)methyl](2-fluoroethyl)amino}furan-2(5H)-thione, has the formula

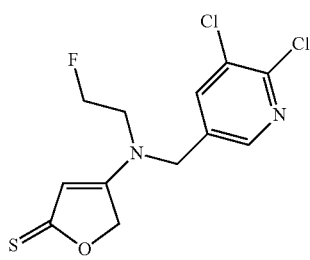 [SMILES: FCCN(Cc1cnc(Cl)c(Cl)c1)C1=CC(=S)OC1]

compound (I-15), 4-{[(5,6-dichloropyrid-3-yl)methyl](2-fluoroethyl)amino}furan-2(5H)-thione, has the formula

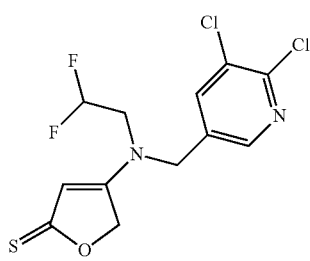

compound (I-16), 4-{[(6-bromo-5-fluoropyrid-3-yl)methyl](2,2-difluoroethyl)amino}furan-2(5H)-thione, has the formula

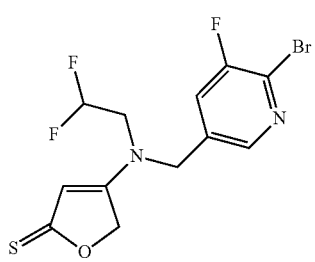 [SMILES: Fc1cc(CN(CC(F)F)C2=CC(=S)OC2)cnc1Br]

compound (I-17), 4-{[(6-chloro-5-fluoropyrid-3-yl)methyl](2,2-difluoroethyl)amino}furan-2(5H)-thione, has the formula

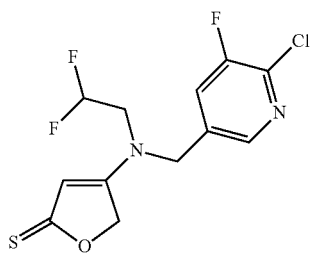 [SMILES: Fc1cc(CN(CC(F)F)C2=CC(=S)OC2)cnc1Cl]

compound (I-18), 4-{[(2-chloro-2,3-dihydro-1,3-thiazol-5-yl)methyl](methyl)amino}furan-2(5H)-thione, has the formula

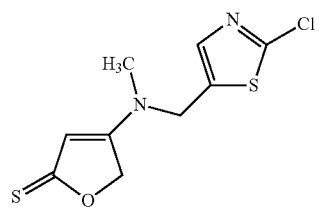

compound (I-19), 4-[methyl(pyrid-3-ylmethyl)amino]furan-2(5H)-thione, has the formula

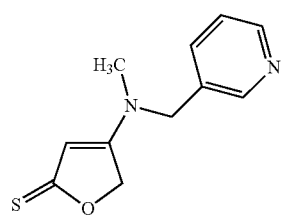

compound (I-20), 4-{cyclopropyl[(6-fluoropyrid-3-yl)methyl]amino}furan-2(5H)-thione, has the formula

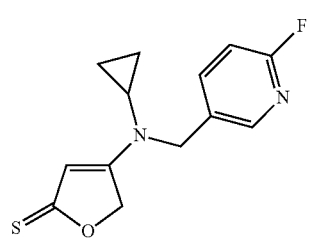 [SMILES: Fc1ccc(CN(C2=CC(=S)OC2)C2CC2)cn1]

compound (I-21), 4-(methyl{[6-(trifluoromethyl)pyrid-3-yl]methyl}amino)furan-2(5H)-thione, has the formula

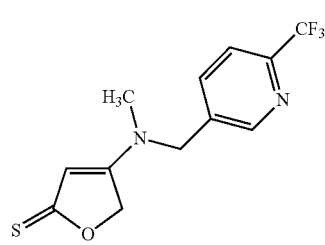 [SMILES: CN(Cc1ccc(C(F)(F)F)nc1)C1=CC(=S)OC1]

compound (I-22), 4-(cyclopropyl{[6-(trifluoromethyl)pyrid-3-yl]methyl}amino)furan-2(5H)-thione, has the formula

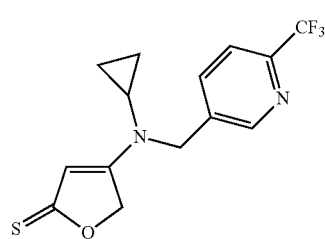 [SMILES: FC(F)(F)c1ccc(CN(C2=CC(=S)OC2)C2CC2)cn1]

compound (I-23), 4-{[(6-chloropyrid-3-yl)methyl](methyl)amino}-5-methylfuran-2(5H)-thione, has the formula

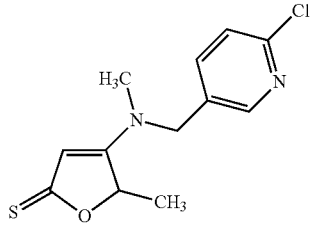 [SMILES: CC1OC(=S)C=C1N(C)Cc1ccc(Cl)nc1]

compound (I-24), 4-{[(6-bromopyrid-3-yl)methyl](methyl)amino}furan-2(5H)-thione, has the formula

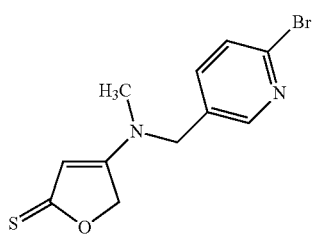 [SMILES: CN(Cc1ccc(Br)nc1)C1=CC(=S)OC1]

compound (I-25), 4-{[(6-chloropyrid-3-yl)methyl](methyl)amino}-3-fluorofuran-2(5H)-thione, has the formula

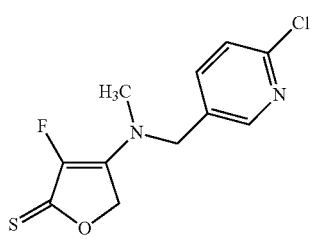 [SMILES: CN(Cc1ccc(Cl)nc1)C1=C(F)C(=S)OC1]

compound (I-26), 4-{[(6-chloropyrid-3-yl)methyl](methoxy)amino}furan-2(5H)-thione, has the formula

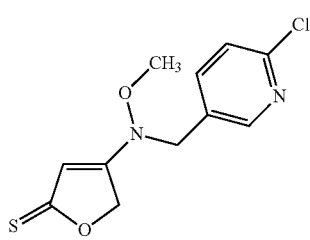 [SMILES: CON(Cc1ccc(Cl)nc1)C1=CC(=S)OC1]

compound (I-27), 4-{[(6-chloropyrid-3-yl)methyl](ethyl)amino}furan-2(5H)-thione, has the formula

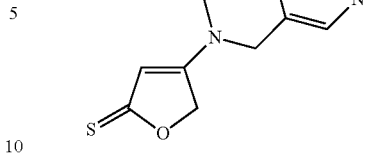

compound (I-28), 4-{[(6-chloropyrid-3-yl)methyl](cyclopropyl)amino}furan-2(5H)-thione, has the formula

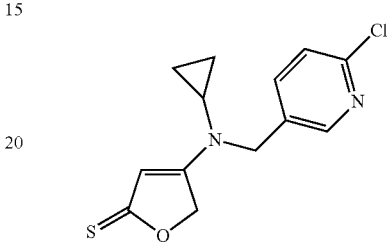

compound (I-29), 4-{allyl[(6-chloropyrid-3-yl)methyl]amino}furan-2(5H)-thione, has the formula

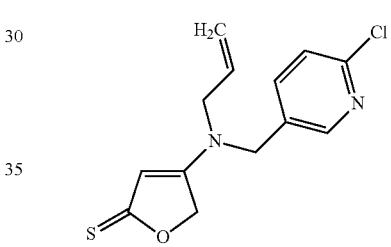

compound (I-30), 4-{[(6-chloropyrid-3-yl)methyl](prop-2-yn-1-yl)amino}furan-2(5H)-thione, has the formula

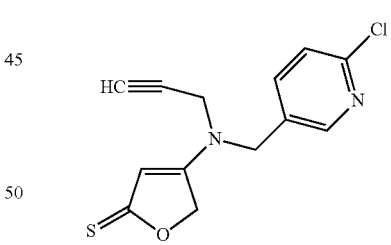

Halogen-substituted radicals, for example haloalkyl, are mono- or polysubstituted up to the maximum possible number of substituents. In the case of polyhalogenation, the halogen atoms can be identical of different. Here, halogen represents fluorine, chlorine, bromine or iodine, in particular fluorine, chlorine or bromine Preference, particular preference or very particular preference is given to compounds which carry the substituents mentioned as being preferred, particularly preferred or very particularly preferred, respectively.

Saturated or unsaturated hydrocarbon radicals such as alkyl or alkenyl can in each case be straight-chain or branched as far as this is possible, including in combination with heteroatoms, such as, for example, in alkoxy.

Optionally substituted radicals can be mono- or polysubstituted, where in the case of polysubstitution the substituents can be identical of different.

The general or preferred radical definitions or illustrations given above apply both to the end products and, correspondingly, to precursors and intermediates. These radical definitions can be combined with one another as desired, i.e. including combinations between the respective preferred ranges.

Preference according to the invention is given to compounds of the formula (I) which contain a combination of the meanings listed above as being preferred.

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

If, in the Process 1 according to the invention for preparing the novel compounds of the formula (I), the compound of the formula (II) is, for example, 4-hydroxyfuran-2(5H)-thione and the compound of the formula (III) is N-[6-chloropyridin-3-yl)methyl]-2,2-difluoroethan-1-amine, Preparation Process 1 can be represented by the Reaction Scheme I below:

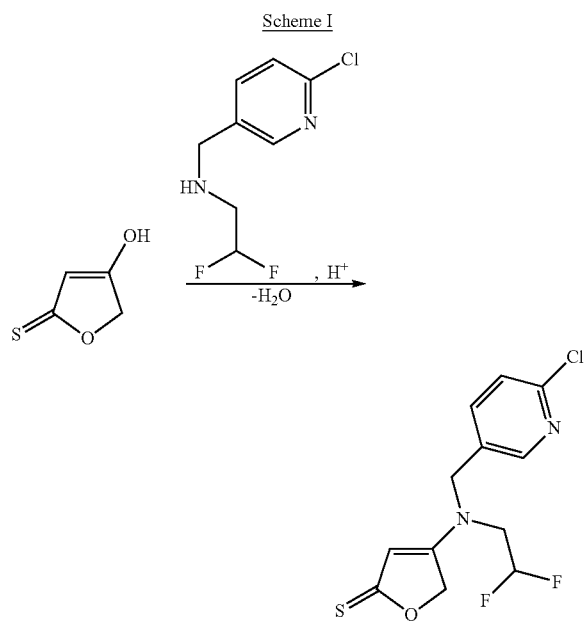

The formula (II) provides a general definition of the compounds required as starting materials for carrying out the Process 1 according to the invention.

In this formula (II), B, $R^2$ and $R^3$ preferably represent those radicals which have already been mentioned in connection with the description of the compounds of the formula (I) according to the invention as preferred substituents.

Some of the compounds of the formula (II) can be obtained by methods known from the literature (cf. Scheme II, for example for compounds of the general formula II in which B represents oxygen and $R^1$, $R^2$ each represent hydrogen: 4-hydroxyfuran-2(5H)-thione (R. Labruère et al., Synthesis 24, 4163-4166, 2006) and B represents sulphur and $R^1$, $R^2$ each represent hydrogen: 4-hydroxythiophene-2(5H)-thione (R. Labruère et al., Synthesis 24, 4163-4166, 2006).

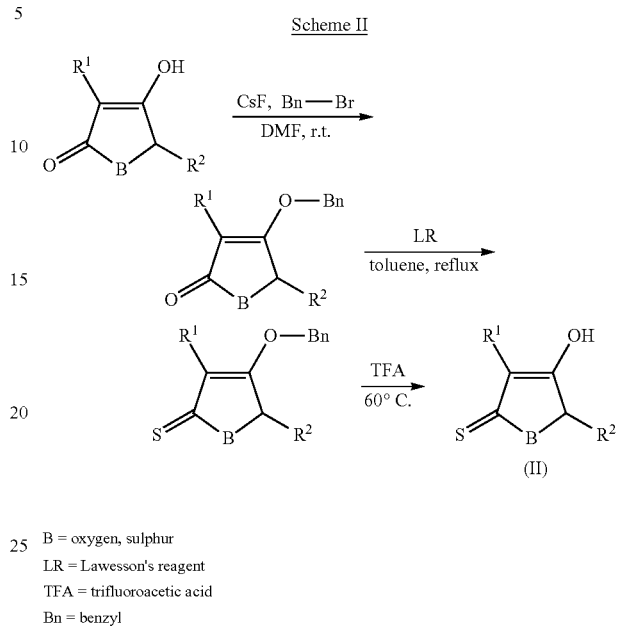

B = oxygen, sulphur
LR = Lawesson's reagent
TFA = trifluoroacetic acid
Bn = benzyl The formula (III) provides a general definition of the compounds furthermore to be used as starting materials for carrying out the Process 1 according to the invention.

In formula (III), A and $R^1$ have the meanings already mentioned in connection with the description of the compounds of the formula (I) according to the invention.

Some of the compounds of the formula (III) can be obtained commercially or by methods known from the literature (cf., for example, S. Patai "The Chemistry of Amino Group", Interscience Publishers, New York, 1968; compounds of the general formula (III) in which $R^1$ represents hydrogen: primary amines, $R^1$ represents haloalkyl, haloalkenyl or halocycloalkyl: secondary amines).

The compounds of the formula (III) can also be prepared from compounds of the formula (VII) (cf. Scheme III further below).

Some of the compounds of the formula (VII) are commercially available, some are known and can be obtained by known methods (for example 2-chloro-5-chloromethyl-1,3-thiazole: DE 3 631 538 (1988), EP 446 913 (1991), EP 780 384 (1997), EP 775 700 (1997), EP 794 180 (1997), WO 9 710 226 (1997); 6-chloro-3-chloromethylpyridine: DE 3 630 046 A1 (1988), EP 373 464 A2 (1990), EP 373 464 A2 (1990), EP 393 453 A2 (1990), EP 569 947 A1 (1993); 6-chloro-3-bromomethylpyridine: I. Cabanal-Duvillard et al., Heterocycl. Commun 5, 257-262 (1999); 6-bromo-3-chloromethylpyridine, 6-bromo-3-hydroxymethylpyridine: U.S. Pat. No. 5,420,270 A (1995); 6-fluoro-3-chloromethylpyridine: J. A. Pesti et al., J. Org. Chem. 65, 7718-7722 (2000); 6-methyl-3-chloromethylpyridine: EP 302389 A2, E. v der Eycken et al., J. Chem. Soc., Perkin Trans 2 5, 928-937 (2002); 6-trifluoromethyl-3-chloromethylpyridine: WO 2004/082616 A2; 2-chloro-5-chloromethylpyrazine: JP 05239034 A2).

General routes for preparing compounds of the formula (VII) are shown in Scheme III.

Scheme III

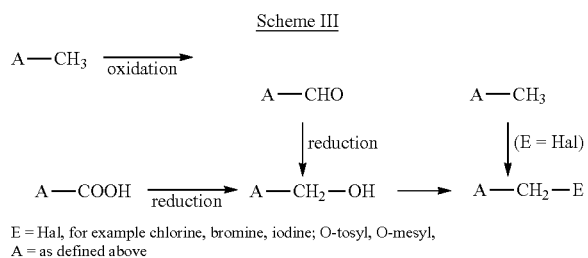

E = Hal, for example chlorine, bromine, iodine; O-tosyl, O-mesyl,
A = as defined above The heterocyclic carboxylic acids (A-COOH), for example, can be converted by methods known from the literature into the corresponding heterocyclic hydroxymethyl compounds (A-CH$_2$—OH) which are then, by methods known from the literature, converted into activated heterocyclic hydroxymethyl compounds (A-CH$_2$-E, E=O-tosyl, O-mesyl) or heterocyclic halomethyl compounds (A-CH$_2$-E, E=Hal). The latter can also be obtained from the corresponding methyl group-containing heterocycles (A-CH$_3$) using suitable halogenating agents known from the literature.

To prepare compounds of the formula (III), it is advantageous to react, for example, compounds of the formula (VII) in which A and E have the meaning mentioned further above with compounds of the formula (V) in which R$^1$ has the meaning mentioned further above, if appropriate in the presence of diluents and if appropriate in the presence of the basic reaction auxiliaries mentioned in Preparation Process 2 (cf. N-alkylation, Scheme IV).

Scheme IV

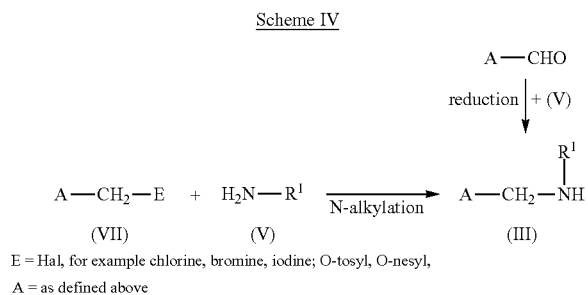

E = Hal, for example chlorine, bromine, iodine; O-tosyl, O-nesyl,
A = as defined above Some of the compounds of the formula (V) are commercially available (cf. for example 2-fluoroethylamine or 2,2-difluoroethylamine), or they can be obtained by methods known from the literature (cf. for example 3-fluoro-n-propylamine: U.S. Pat. No. 6,252,087 B1; 3,3-difluoroprop-2-enylamine hydrochloride: WO 2001/007414 A1; 3,3-dichloroprop-2-enylamine: DE 2747814).

However, alternatively and in certain cases it is also possible to prepare compounds of the formula (III) from the corresponding aldehydes (A-CHO) and compounds of the formula (V) by reductive amination (cf. Houben-Weyl, Methoden der Organischen Chemie [Methods of Organic Chemistry], Vol. XI/1, Georg Thieme Verlag Stuttgart, p. 602). Some of the aldehydes (A-CHO) are commercially available (cf. for example 6-chloronicotinaldehyde, 6-fluoronicotinaldehyde, 6-bromonicotinaldehyde, 2-chloro-1,3-thiazole-5-carbaldehyde), or they can be obtained by methods known from the literature (cf., for example, 6-methylnicotinaldehyde: EP 104876 A2; 2-chloropyrazine-5-carboxaldehyde: DE 3314196 A1).

The preparation of the compounds of the general formula (III) is also described, for example, in WO 2007/115644, WO 2007/115646 or WO 2008/009360 A2 and can be carried out in an analogous manner.

In general, it is advantageous to carry out the Preparation Process 1 according to the invention in the presence of diluents. Diluents are advantageously employed in an amount such that the reaction mixture remains readily stirrable during the entire process. Suitable diluents for carrying out the Process 1 according to the invention are all organic solvents which are inert under the reaction conditions. These diluents are mentioned in the description of Process 2 according to the invention.

It is, of course, also possible to carry out the Process 1 according to the invention in mixtures of the solvents and diluents mentioned.

The preparation of compounds of the formula (I) according to Preparation Process 1 is preferably carried out by reacting compounds of the formula (II) in the presence of compounds of the formula (III), if appropriate in the presence of an acidic auxiliary and if appropriate in one of the diluents mentioned.

Known acidic auxiliaries are, for example, inorganic acids, such as hydrochloric acid, hydrobromic acid, nitric acid, sulphuric acid, phosphoric acid, or organic acids, such as formic acid, acetic acid, propionic acid, malonic acid, oxalic acid, fumaric acid, adipic acid, stearic acid, tartaric acid, lactic acid, oleic acid, methanesulphonic acid, benzenesulphonic acid or toluenesulphonic acid.

The preparation of compounds of the formula (I) according to Preparation Process 1 is particularly preferably carried out by reacting compounds of the formula (II) in the presence of compounds of the formula (III) in an acidic auxiliary which simultaneously acts as diluent.

A suitable acidic auxiliary which simultaneously acts as diluent is, for example, acetic acid.

The reaction time is generally from 10 minutes to 20 days. The reaction is generally carried out at temperatures between −10° C. and +150° C., preferably between +10° C. and 100° C., particularly preferably at room temperature.

In principle, the reaction can be carried out at atmospheric pressure. Advantageously, the reaction is carried out at atmospheric pressure or at pressures of up to 15 bar and, if appropriate, under an atmosphere of protective gas (nitrogen, helium or argon).

For carrying out the Process 1 according to the invention, in general from 0.5 to 5.0 mol, preferably from 0.7 to 3.5 mol, particularly preferably from 1.0 to 3.0 mol of amino compound of the general formula (III) are employed per mole of the compound of the general formula (II).

However, alternatively, by selecting a suitable solvent and diluent (mentioned under Process 2), it is preferably also possible to operate under reaction conditions which allow water to be separated off or to be removed, for example with the aid of a water separator.

Preferred diluents for carrying out the Process 1 according to the invention are aromatic hydrocarbons such as benzene, toluene, chlorbenzene, bromobenzene, nitrobenzene or xylene, in particular benzene and toluene.

Furthermore, when carrying out the Process 1 according to the invention in an organic solvent, it is generally possible to add catalytic amounts of one of the acidic auxiliaries mentioned further above.

Suitable acidic auxiliaries are, for example, p-toluenesulphonic acid or acetic acid.

After the reaction has gone to completion, the entire reaction mixture is concentrated. The products obtained after work-up can be purified in a customary manner by recrystallization, distillation under reduced pressure or column chromatography (cf. also the Preparation Examples).

If, in the Process 2 according to the invention for preparing the novel compounds of the formula (I), the compound of the formula (Ia) used is, for example, 4-[[(6-chloropyridin-3-yl)methyl]-amino]furan-2(5H)-thione and the compound of the formula (IV) is 3-bromo-1,1-dichloroprop-1-ene, the Preparation Process 2 can be represented by Reaction Scheme V below:

Scheme V

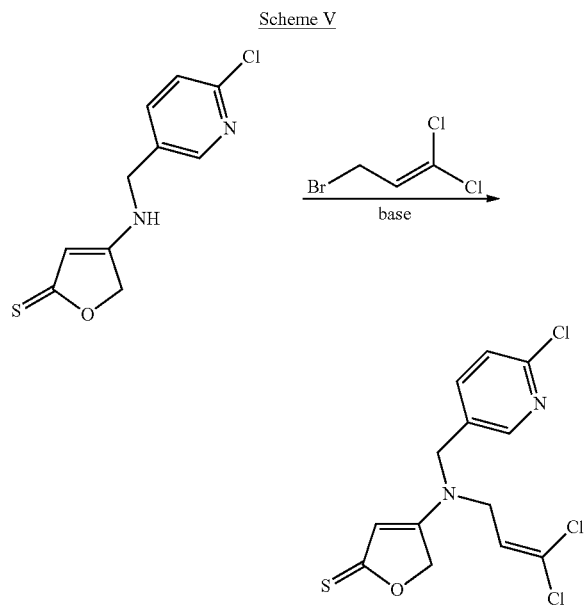

The formula (Ia) provides a general definition of the compounds required as starting materials for carrying out the Process 2 according to the invention.

In this formula (Ia), A, B, $R^2$ and $R^3$ preferably represent those radicals which have already been mentioned in connection with the description of the compounds of the formula (I) according to the invention as preferred substituents.

The compounds of the formula (Ia) can be obtained by Preparation Process 1, described further above, for example by reacting compounds of the formula (II) with compounds of the formula (III) in which $R^1$ represents hydrogen.

4-[[(6-Chloropyridin-3-yl)methyl]amino]furan-2(5H)-thione, used as starting material in particular for carrying out the Process 2 according to the invention, is known from EP 0 539 588 A1.

The formula (IV) provides a general definition of the compounds to be used in particular as starting materials for carrying out the Process 2 according to the invention.

In formula (IV), E and $R^1$ have the meaning already mentioned in connection with the description of the compounds of the general formula (I) according to the invention.

Some of the compounds of the formula (IV) are commercially available (cf., for example, chlorodifluoromethane, 1-bromo-2-fluoroethane, 2-bromo-1,1-difluoroethane, 2-bromo-1-chloro-1-fluoroethane, 1-bromo-3-fluoropropane, 3-bromo-1,1-difluoroprop-1-ene, or they can be obtained by methods known from the literature (cf. for example 3-bromo-1,1-dichloroprop-1-ene: WO 8800183 A1 (1988); compounds of the formula (IV) in which E represents halogen, such as chlorine, bromine and iodine: Houben-Weyl, Methoden der Organischen Chemie, vol. V/3, Georg Thieme Verlag Stuttgart, p. 503 and vol. V/4 p. 13, 517; $E^1$ represents mesylate: Crossland, R. K., Servis, K. L. J. Org. Chem. (1970), 35, 3195; E represents tosylate: Roos, A. T. et al., Org. Synth., Coll. Vol. I, (1941), 145; Marvel, C. S., Sekera, V. C. Org. Synth., Coll. Vol. III, (1955), 366.

In general, it is advantageous to carry out the Preparation Process 2 according to the invention in the presence of diluents and in the presence of basic reaction auxiliaries.

Diluents are advantageously employed in an amount such that the reaction mixture remains readily stirrable during the entire process. Diluents suitable for carrying out the Process 2 according to the invention are all organic solvents which are inert under the reaction conditions.

Examples which may be mentioned are: halogenated hydrocarbons, in particular chlorinated hydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, n-butyl ether, ani-sole, phenetol, cyclohexyl methyl ether, dimethyl ether, diethyl ether, dipropyl ether, diisopropyl ether, di-n-butyl ether, diisobutyl ether, diisoamyl ether, ethyleneglycol dimethyl ether, tetrahydrofuran, dioxane, dichlorodiethyl ether and ethylene oxide and/or propylene oxide polyethers; amines, such as trimethylamine, triethylamine, tripropylamine, tributylamine, N-methylmorpholine, pyridine and tetramethylenediamine; nitrated hydrocarbons such as nitromethane, nitroethane, nitropropane, nitrobenzene, chloronitrobenzene, o-nitrotoluene; nitriles, such as acetonitrile, propionitrile, butyronitrile, isobutyronitrile, benzonitrile, m-chlorobenzonitrile and also compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones, such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons, such as pentane, hexane, heptane, octane, nonane and industrial hydrocarbons, for example white spirits having components of boiling points in the range of, for example, from 40° C. to 250° C., cymene, petroleum fractions within a boiling point range of from 70° C. to 190° C., cyclohexane, methylcyclohexane, petroleum ether, ligroin, octane, benzene, toluene, chlorobenzene, bromobenzene, nitrobenzene, xylene; esters, such as methyl acetate, ethyl acetate, butyl acetate, isobutyl acetate, and also dimethyl carbonate, dibutyl carbonate, ethylene carbonate; amides, such as hexamethylphosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-1,4-diformylpiperazine; ketones, such as acetone, acetophenone, methyl ethyl ketone, methyl butyl ketone.

Diluents are advantageously employed in an amount such that the reaction mixture remains readily stirrable during the entire process.

Preferred diluents for carrying out the Process 2 according to the invention are ethers such as methyl tert-butyl ether, n-butyl ether, anisole, phenetol, cyclohexyl methyl ether, diisopropyl ether, diisobutyl ether, diisoamyl ether, ethylene glycol dimethyl ether, tetrahydrofuran, dioxane, dichlorodiethyl ether and polyethers of ethylene oxide and/or propylene oxide, amides, such as hexamethylenephosphoric triamide, formamide, N-methylformamide, N,N-dimethylformamide, N,N-dipropylformamide, N,N-dibutylformamide, benzene, toluene, chlorobenzene, bromobenzene, nitrobenzene, xylene; ketones, such as acetone, acetophenone, methyl ethyl ketone or methyl butyl ketone.

It is, of course, also possible to carry out the process according to the invention in mixtures of the solvents and diluents mentioned.

However, preferred diluents for carrying out the process according to the invention are ethers, such as methyl tert-butyl ether or cyclic ethers, such as tetrahydrofuran and dioxane, amides, such as N,N-dimethylformamide, aromatic hydrocarbons, such as benzene or toluene; ketones, such as acetone, methyl ethyl ketone or methyl butyl ketone.

Suitable basic reaction auxiliaries for carrying out the Process 2 according to the invention are all suitable acid binders, such as amines, in particular tertiary amines, and also alkali metal and alkaline earth metal compounds.

Examples which may be mentioned are the hydroxides, hydrides, oxides and carbonates of lithium, sodium, potassium, magnesium, calcium and barium, furthermore other basic compounds, such as amidine bases or guanidine bases, such as 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo-[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, isoquinoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethyldiamine.

Preference is given to using hydrides of lithium or sodium.

The reaction time is generally from 10 minutes to 48 hours. The reaction is carried out at temperatures between −10° C. and +200° C., preferably between +10° C. and 180° C., particularly preferably between 60° C. and 140° C. In principle, it is possible to operature under atmospheric pressure. Preferably, the reaction is carried out at atmospheric pressure or at pressures of up to 15 bar and, if appropriate, under an atmosphere of protective gas (nitrogen, helium or argon).

To carry out the Process 2 according to the invention, in general from 0.5 to 4.0 mol, preferably from 0.7 to 3.0 mol, particularly preferably from 1.0 to 2.0 mol of an alkylating agent of the formula (IV) are employed per mole of the compound of the formula (II).

After the reaction has gone to completion, the entire reaction mixture is concentrated. The products obtained after work-up can be purified in a customary manner by recrystallization, distillation under reduced pressure or column chromatography (cf. also the Preparation Examples).

If, in the Process 3 according to the invention for preparing the novel compounds of the formula (I), in a first reaction step the compound of the formula (II) employed is, for example, 4-hydroxyfuran-2(5ll)-thione and the compound of the formula (V) is 2-fluoroethylamine, and in a second reaction step the compound of the formula (VI) formed is 4-[(2-fluoroethyl)amino]furan-2(5H)-thione, which is N-alkylated with compounds of the formula (VII), for example 2-chloro-5-(chloromethyl)pyridine, the Preparation Process 3 can be represented by Reaction Scheme VI below:

Scheme VI

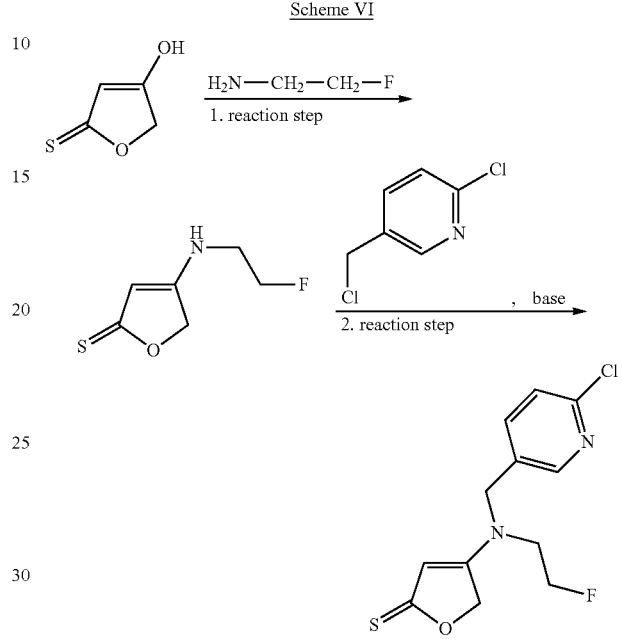

The formula (II) provides a general definition of the compounds required as starting materials for carrying out the Process 3 according to the invention; these compounds have already been described in more detail in Process 1 mentioned further above.

The formula (V) provides a general definition of the compounds further to be used as starting materials for carrying out the Process 3 according to the invention.

In formula (V), $R^1$ has the meaning already mentioned in connection with the description of the compounds of the formula (I) according to the invention.

In many cases, some of the amino compounds of the formula (V) can be obtained commercially (cf., for example, 2-fluoroethylamine or 2,2-difluoroethylamine) or in a manner known per se by the "Leuckart-Wallach reaction" (for example 2-fluoroethylamine: U.S. Pat. No. 4,030,994 (1977); compounds of the formula (V) in which $R^1$ represents alkyl, primary amines: cf., for example, Houben-Weyl, Methoden der Organischen Chemie, Vol. XI/1, 4. Ed. 1957, Georg Thieme Verlag Stuttgart, p. 648; M. L. Moore in "The Leuckart Reaction" in: Organic Reactions, Vol. 5, 2. Ed. 1952, New York, John Wiley & Sons, Inc. London) (cf., for example, also 3-fluoro-n-propylamine: U.S. Pat. No. 6,252,087 B1; 3,3-difluoroprop-2-enylamine hydrochloride: WO 2001/007414 A1; 3,3-dichloroprop-2-enylamine: DE 2747814); 2-chloro-2-fluorocyclopropylamine, 2,2-dichlorocyclopropylamine: K. R. Gassen, B. Baasner, J. Fluorine Chem. 49, 127-139, 1990).

Alternatively, certain amino compounds of the formula (Va) in which $R^1$ represents $CH_2$—R' (R'=halogen-containing radical; halogen=fluorine or chlorine) can also be obtained by reduction of halogenated carboxamides (VIII) in the presence of suitable reducing agents (Reaction Scheme VII).

Scheme VII

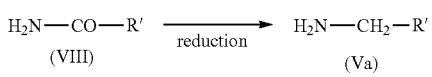

R' = halogen-containing radical

A preferred reducing agent is, for example, the known borane/dimethyl sulphide complex (cf. also the preparation of 2-chloro-2-fluoroethan-1-amine from commercially available 2-chloro-2-fluoroacetamide).

The formula (VII) provides a general definition of the compounds further to be used as starting materials for carrying out the Process 3 according to the invention.

In formula (VII), E and A have the meaning already mentioned in connection with the description of the compounds of the formula (I) according to the invention.

As already mentioned further above, some of the compounds of the general formula (VII) are commercially available, some are known, or they can be obtained by known methods.

In general, it is advantageous to carry out the first reaction step of the Preparation Process 3 according to the invention in the presence of diluents and, if appropariate, in the presence of an acidic auxiliary.

Acidic auxiliaries which may be used are, for example, the acidic auxiliaries mentioned further above under Process 1.

Diluents are advantageously employed in an amount such that the reaction mixture remains readily stirrable during the entire process. Suitable diluents for carrying out the Process 3 according to the invention are all inert organic solvents.

Preferred diluents for carrying out the first reaction step of the Process 3 according to the invention are aromatic hydrocarbons, such as benzene, toluene, chlorobenzene, bromobenzene, nitrobenzene or xylene, but in particular benzene and toluene.

Particularly preferably, the preparation of compounds of the formula (I) according to Preparation Process 3 is carried out by reacting, when carrying out the first reaction step, compounds of the formula (II) in the presence of compounds of the formula (V) in an acidic auxiliary which simultaneously acts as diluent.

A suitable acidic auxiliary which simultaneously acts as diluent is, for example, acetic acid.

The reaction time is generally from 10 minutes to 20 days.

In the second reaction step, the compounds of the formula (VI) are N-alkylated with compounds of the formula (VII).

In general, it is advantageous to carry out the second reaction step of the Preparation Process 3 according to the invention in the presence of diluents and in the presence of basic reaction auxiliaries, such as, for example, sodium hydride.

Diluents suitable for this reaction step are, for example, ethers, such as tetrahydrofuran or dioxane.

Diluents are advantageously employed in an amount such that the reaction mixture remains readily stirrable during the entire process.

The reaction time is generally from 10 minutes to 48 hours.

The reaction is carried out at temperatures between −10° C. and +200° C., preferably between +10° C. and 180° C., particularly preferably between 60° C. and 140° C. The reaction is preferably carried out under reaction conditions which allow water to be separated off or to be removed, for example with the aid of a water separator.

After the reaction has gone to completion, the entire reaction mixture is concentrated. The products obtained after work-up can be purified in a customary manner by recrystallization, distillation under reduced pressure or column chromatography (cf. also the Preparation Examples).

Alternatively and if appropriate, to prepare the novel compounds of the formula (I) in which A, B and $R^1$ to $R^3$ have the meanings mentioned further above, it is also possible to employ the compounds of the formula (IX) as precursors in the presence of a suitable sulphurizing agent according to Scheme VIII:

Scheme VIII

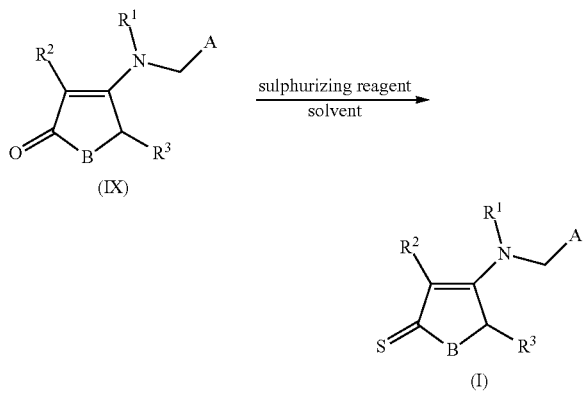

The compounds of the general formula (IX) are known and can be obtained according to EP 0 539 588 A1, WO 2007/115643, WO 2007/115644 or WO 2007/115646.

A large number of different sulphurizing agents are described in the literature, such as, for example, hydrogen sulphide ($H_2S$), hydrogen sulphide/hydrogen chloride ($H_2S$/HCl), hydrogen persulphide/hydrogen chloride ($H_2S_2$/HCl), di(diethylaluminium) sulphide [$(Et_2Al)_2S$], polymeric ethylaluminium sulphide [$(EtAlS)_n$], silicon disulphide ($SiS_2$), diboron trisulphide ($B_2S_3$), phosphorus pentachloride/dialuminium trisulphide/sodium sulphate ($PCl_5$/$Al_2S_3$/$Na_2SO_4$), sodium sulphide/sulphuric acid ($Na_2S$/$H_2SO_4$), diphosphorus pentasulphide ($P_2S_5$), diphosphorus pentasulphide/pyridine ($P_2S_5$/Py), diethylthiocarbamoyl chloride, diphosphorus pentasulphide/triethylamine ($P_2S_5$/$NEt_3$), diphosphorus pentasulphide/n-butyllithium ($P_2S_5$/n-BuLi), diphosphorus pentasulphide/sodium bicarbonate ($P_2S_5$/$NaHCO_3$; "Scheeren's Reagent", formation of $Na^{2-}[P_4S_{10}O]^{2-}$), diphosphorus pentasulphide/methanol ($P_2S_5$/MeOH), SCN—CO-OEt, $PSCl_x$. $(NMe_2)_{3-X}$ (X=0-3), bis(1,5-cyclooctanediylboryl)sulphide [$(9-BBN)_2S$] as sulphurizing agent or as phosphorus pentasulphide substitute, 2,4-bis(methylthio)-1,3,2,4-dithiadiphosphetane-2,4-disulphide "Davy Reagent Methyl" (DR-Me), 2,4-bis(ethylthio)-1,3,2,4-dithiadiphosphetane-2,4-disulphide "Davy Reagent Ethyl" (DR-Et), 2,4-bis(p-tolylthio)-1,3,2,4-dithiadiphosphetane 2,4-disulphide "Davy Reagent p-tolyl or Heimgartner Reagent" (DR-T), 2,4-bis(4-phenoxyphenyl)-2,4-dithioxo-1,3,2,4-dithiadiphosphetane "Belleau's Reagent (BR)", 2,4-bis(4-methoxyphenyl)-2,4-dithioxo-1,3,2,4-dithiadiphosphetane "Lawesson's Reagent (LR)" (cf. Davy Reagent: H. Heimgartner et al., *Helv. Chim. Acta* 70, 1987, p. 1001; Belleau's Reagent: *Tetrahedron* 40, 1984, p. 2047; *Tetrahedron* 40, 1984, p. 2663; *Tetrahedron Letters* 24, 1983, p. 3815; I. Thomson et al., *Org. Synth.* 62, 1984, p. 158 and the literature cited therein; D. Brillon *Synthetic Commun.* 20, 1990, p. 3085 and the literature cited therein; selective thionation of oligopeptides; K. Clausen et al., *J. Chem. Soc., Perkin Trans I* 1984, p. 785; O. E. Jensen et al., *Tetrahedron* 41, 1985, p. 5595; "Lawesson's Reagent, (LR)": R. A. Cherkasov et al., *Tetrahedron* 41, 1985, p. 2567; K. Clausen et al., *Tetrahedron* 37, 1981, p. 3635, M. P. Cava et al., *Tetrahedron* 41, 1985, p. 5061; diboryl sulphide: *Liebigs Ann. Chem.* 1992, p. 1081 and literature cited therein; Metzner et al. in *Sulphur Reagents in Organic Synthesis*, B. Harcourt (ed.), London 1994, Academic Press, p. 44-45).

Alternative possibilities are also reaction sequences such as, for example, O-alkylation with $R_3O^+BF_4^-$ (R=methyl, ethyl) (H. Meerwein et al., *Justus Liebigs Ann. Chem.* 641, (1961) p. 1) and subsequent reaction of the intermediates with anhydrous NaSH (R. E. Eibeck, *Inorg. Synth.* 7, 1963, p. 128), the in-situ formation of chloroiminium salts and subsequent reaction with tetrathiomolybdates, in particular benzyltriethylammonium tetrathiomolybdate [(Ph-CH$_2$—NEt$_3$)$_2$ MoS$_4$] (*Tetrahedron Lett.* 36, 1995, p. 8311) or hexamethyldisilathiane (TMS$_2$S) (TMS=trimethylsilyl; P. L. Fuchs et al., *J. Org. Chem.* 59, 1994, p. 348).

Preferred sulphurizing agents are phosphorus reagents, such as, for example, diphosphorus pentasulphide ($P_2S_5$), diphosphorus pentasulphide/pyridine ($P_2S_5$/Py), diphosphorus pentasulphide/triethylamine ($P_2S_5$/NEt$_3$), diphosphorus pentasulphide/sodium bicarbonate ($P_2S_5$/NaHCO$_3$ "Scheeren's Reagent") or, particularly preferably, 2,4-bis(4-methoxyphenyl)-2,4-dithioxo-1,3,2,4-dithiadiphosphetane "Lawesson's Reagent (LR)", 2,4-bis(4-phenoxyphenyl)-2,4-dithioxo-1,3,2,4-dithiadiphosphetane "Belleau's Reagent (BR)" or 2,4-bis(4-phenylthiophenyl)-2,4-dithioxo-1,3,2,4-dithiadiphosphetane.

To prepare the compounds of the formula (I) in which $R^2$ represents halogen, it is alternatively also possible to react compounds of the formula (I) in which $R^2$ represents hydrogen with halogenating agents in the presence of basic reaction auxiliaries according to Reaction Scheme (IX).

Scheme IX:

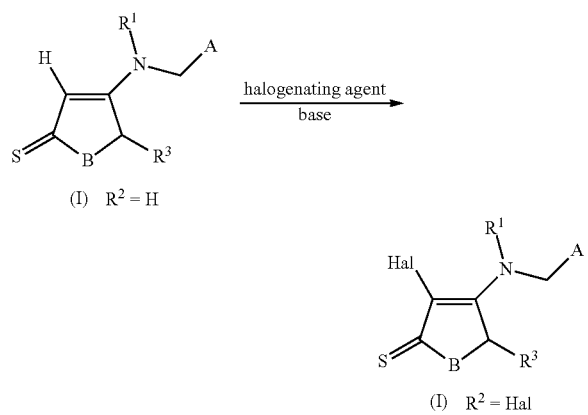

halogenating agent: Selectfluor (for Hal = F),
N-chlorosuccinimide (NCS for Hal = Cl),
N-bromosuccinimide (NBS for Hal = Br).

In the compounds of the formula (I) required as starting materials, A, B, $R^1$ and $R^3$ have the meaning mentioned further above, the substituent $R^2$ represents hydrogen.

These compounds of the formula (I) can be obtained by the Preparation Processes 1 to 3 mentioned further above.

In general, it is advantageous to carry out the halogenation in the presence of diluents. Diluents are advantageously employed in an amount such that the reaction mixture remains readily stirrable during the entire process. Suitable diluents for carrying out the halogenation are all organic solvents which are inert under the reaction conditions.

Suitable halogenating agents for carrying out the process according to the invention are all suitable halogenating agents, for example N-halo compounds.

Examples which may be mentioned are N-haloamines, such as 1-chloromethyl-4-fluorodiazonia-bicyclo[2.2.2]octanebis(tetrafluoroborate) (Selectfluor®), N,N-dihaloamines, N-halocarboxamides, N-halocarbamic esters, N-halourea, N-halosulphonylamides, N-halodisulphonylamides, N-halosulphonylimides, such as N-fluorobis[(trifluoromethyl)sulphonyl]imide and N-halocarboxylic acid diamides, such as N-chlorophthalimide, N-bromophthalimide, N-iodophthalimide, N-chloro-succinimide (NCS), N-bromosuccinimide (NBS), N-bromosaccharin or N-iodosuccinimide.

Preferred halogenating agents for carrying out the halogenation are the N-halocarboxylic acid diamides or 1-chloromethyl-4-fluorodiazoniabicyclo[2.2.2]octanebis(tetrafluoroborate) (Selectfluor®).

Preferred diluents for carrying out the halogenation are nitriles, such as acetonitrile, propionitrile, butyronitrile, isobutyronitrile, benzonitrile, m-chlorobenzonitrile.

It is also possible to use mixtures of the diluents and solvents mentioned for the process according to the invention.

Particularly preferred diluents for carrying out the process according to the invention are nitriles, such as acetonitrile, propionitrile or butyronitrile.

The reaction time in this process is generally from 10 minutes to 48 hours.

The reaction is carried out at temperatures between −10° C. and +100° C., preferably between 0° C. and 60° C., particularly preferably between 10° C. and room temperature.

After the reaction has gone to completion, the entire reaction mixture is concentrated. The products obtained after work-up can be purified in a customary manner by recrystallization, distillation under reduced pressure or column chromatography (cf. also the Preparation Examples).

If appropriate, the compounds of the formula (I) can be present in different polymorphic forms or as a mixture of different polymorphic forms. Both the pure polymorphs and the polymorph mixtures are provided by the invention and can be used according to the invention.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta*

*oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane*

*antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose, natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself.

When used as insecticides, the active compounds according to the invention can furthermore be present in their commercially available formulations and in the use forms, prepared from these formulations, as mixtures with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injecting and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes and slugs and snails by virtue of toxins formed in the plants, in particular those formed in the plants by the genetic material from *Bacillus* thuringiensis (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMF® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal application, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of from 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of domestic insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for scattering or in bait stations.

PREPARATION EXAMPLES

Example 1

4-{[(6-Chloropyridin-3-yl)methyl](2,2-difluoroethyl)amino}furan-2(5H)-thione

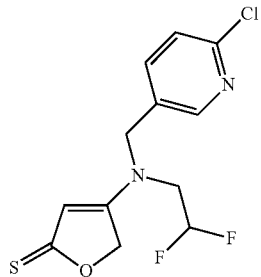 [SMILES: FC(F)CN(Cc1ccc(Cl)nc1)C1=CC(=S)OC1]

105 mg (0.506 mmol) of N-[(6-chloropyridin-3-yl)methyl]-2,2-difluoroethanamine (which can be prepared according to: WO 2007/115644 A1, WO 2008/009360 A2) were added to 20 mg (0.169 mMol) of 4-hydroxyfuran-2(5H)-thione (known from: R. Labruère et al., Synthesis 4163-4166, 2006) in 0.5 ml of acetic acid, and the mixture was stirred at room temperature for 14 days. Concentration under reduced pressure and purification of the residue by preparative HPLC (RP18, CH$_3$CN—H$_2$O) gave 15 mg (yield: 28.8% of theory) of 4-{[(6-chloropyridin-3-yl)methyl](2,2-difluoroethyl)amino}furan-2(5H)-thione.

$^1$H-NMR (CDCl$_3$): δ [ppm]=3.54 (td, 2H), 4.53 (s, 2H), 5.18 (s, 2H), 5.75 (s, 1H), 5.97 (t, 1H), 7.40 (d, 1H), 7.53 (dd, 1H), 8.29 (d, 1H).

$^{13}$C-NMR (CDCl$_3$): δ [ppm]=52.6, 53.4, 75.0, 104.2 (br), 112.9 (br), 125.0, 128.4, 137.4, 148.5, 152.2, 169.5 (br), 212.3.

BIOLOGICAL EXAMPLES

Example No. 1

Phaedon Test (PHAECO Spray Treatment)

Solvents: 78 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of Chinese cabbage leaves (*Brassica pekinensis*) are sprayed with an active compound preparation of the desired concentration and, after drying, populated with larvae of the mustard beetle (*Phaedon cochleariae*).

After the desired period of time, the effect in % is determined 100% means that all beetle larvae have been killed; 0% means that none of the beetle larvae have been killed.

In this test, for example, the following compounds of the Preparation Examples showed an activity of ≥80% at an application rate of 500 g/ha: Ex. No. 1

Example No. 2

Myzus Test (MYZUPE Spray Treatment)

Solvents: 78 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of Chinese cabbage leaves (*Brassica pekinensis*) which are infested by all stages of the green peach aphid (*Myzus persicae*) are sprayed with a preparation of active compound of the desired concentration.

After the desired period of time, the effect in % is determined 100% means that all aphids have been killed; 0% means that none of the aphids have been killed.

In this test, for example, the following compounds of the Preparation Examples showed an activity of ≥80% at an application rate of 500 g/ha: Ex. No. 1

The invention claimed is:

1. A compound of formula (I)

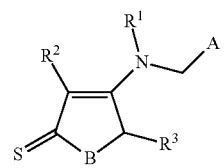

in which

A represents pyrid-2-yl or pyrid-4-yl or represents pyrid-3-yl which is optionally substituted in the 6-position by fluorine, chlorine, bromine, methyl, trifluoromethyl or trifluoromethoxy, or A represents a radical

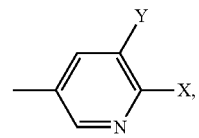

in which

X represents halogen, alkyl or haloalkyl,

Y represents halogen, alkyl, haloalkyl, haloalkoxy, azido or cyano,

B represents oxygen,

R$^1$ represents haloalkyl or halocycloalkyl,

R$^2$ represents hydrogen and

R$^3$ represents hydrogen.

2. A composition comprising at least one compound of the formula (I) according to claim 1 and one or more customary extenders and/or surfactants.

3. A method for controlling pests selected from insects, arachnids or nematodes comprising applying a compound of the formula (I) according to claim 1 to the pest and/or a habitat thereof to thereby control the pests.

4. A plant protection agent comprising a compound of formula (I).

5. A plant protection agent comprising a composition of claim 2.

6. A method for controlling pests selected from insects, arachnids or nematodes comprising applying a composition according to claim 2 to the pest and/or a habitat thereof to thereby control the pests.

7. A compound of the formula (I) according to claim 1, wherein the compound is 4-{[(6-Chloropyridin-3-yl)methyl](2,2-difluoroethyl)amino}furan-2(5H)-thione.

8. A compound of the formula (I) according to claim 1, wherein A represents pyrid-2-yl.

9. A compound of the formula (I) according to claim 1, wherein A represents pyrid-4-yl.

10. A compound of the formula (I) according to claim 1, wherein A represents pyrid-3-yl.

11. A compound of the formula (I) according to claim 1, wherein A represents pyrid-2-yl or pyrid-4-yl or represents pyrid-3-yl which is substituted in the 6-position by fluorine, chlorine, bromine, methyl, trifluoromethyl or trifluoromethoxy.

12. A compound of the formula (I) according to claim 1, wherein A represents a radical
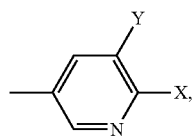
in which
X represents halogen, alkyl or haloalkyl,
Y represents halogen, alkyl, haloalkyl, haloalkoxy, azido or cyano,
B represents oxygen,
$R^1$ represents haloalkyl or halocycloalkyl,
$R^2$ represents hydrogen and
$R^3$ represents hydrogen.
* * * * *